United States Patent [19]
Lawton et al.

[11] Patent Number: 5,114,960
[45] Date of Patent: May 19, 1992

[54] SUBSTITUTED ISOXAZOLE DERIVATIVES

[75] Inventors: Geoffrey Lawton, Hitchin; John M. Osbond, Hatfield; Christopher R. Self, Hitchin, all of England

[73] Assignee: Hoffmann-La Roche Inc., Nutley, N.J.

[21] Appl. No.: 543,905

[22] Filed: Jun. 26, 1990

[30] Foreign Application Priority Data

Jul. 20, 1989 [GB] United Kingdom ............... 8916563
May 11, 1990 [GB] United Kingdom ............... 9010591

[51] Int. Cl.$^5$ ............... C07D 261/20; C07D 275/04; A61K 31/42; A61K 31/425
[52] U.S. Cl. ............................. 514/379; 514/373; 544/172; 548/110; 548/207; 548/241; 560/38; 560/39; 568/374
[58] Field of Search .................... 548/241; 514/379

[56] References Cited

U.S. PATENT DOCUMENTS 3,951,999 4/1976 Saunders et al. ............... 548/241
4,774,253 9/1988 Machin et al. .................. 514/374

OTHER PUBLICATIONS

Caramella et al., *Chemical Abstracts*, vol. 80, No. 145034 (1974).
Dinarello, Interleukin-1 and Interleukin-2 Antagonism, Blood, vol. 77, No. 8 (Apr. 15), 1991; pp. 1627-1652.
Wakabayashi, et al., A specific receptor antagonist for interleukin 1 prevents *Eschericia coli*-induced shock in rabbits, The Faseb Journal, vol. 5, p. 338, Mar. 1991.
Ohlsson, et al., Interleukin-1 receptor antagonist reduces mortality from endotoxin shock, Nature, vol. 348, Dec. 6, 1990, p. 550.
Jacobs, et al., Elevated Interleukin-1 Release Human Alveolar Macrophages during the Adult Respiratory Distress Syndrome[1,2], AM Rev Respir Dis 1989; 140:1686-1692.
Pujol, et al., Interleukin-1 Release by Alveolar Macrophages in Asthmatic Patients and Helthy Subjects, Int. Arch Allergy Appl Immunol 1990; 91:207-210.
Mahida, et al., Aminosalicylic acid is a potent inhibitor (List continued on next page.)

*Primary Examiner*—Cecilia Shen
*Assistant Examiner*—E. Bernhardt
*Attorney, Agent, or Firm*—George M. Gould; George W. Johnston; William Krovatin

[57] ABSTRACT

Compounds of the formula

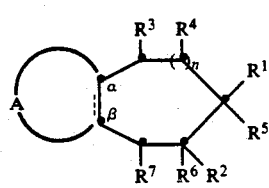

wherein A taken together with the two carbon atoms denoted as α and β is a group of the formula

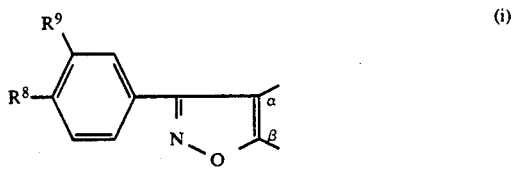

(i)

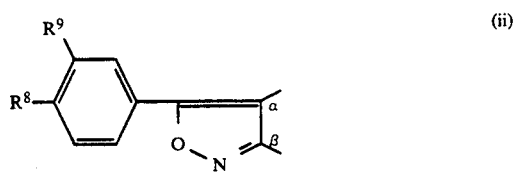

(ii)

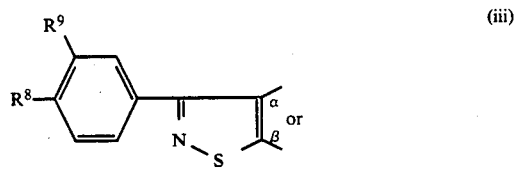

(iii)

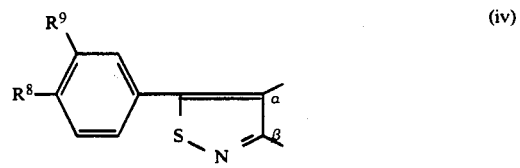

(iv)

and the dotted line is the double bond present in formulas (i) and (iii); and wherein n is zero, 1, 2 or 3, one of $R^1$ and $R^2$ is carboxy or alkoxycarbonyl and the other is hydrogen, $R^3$ is hydrogen, alkyl, alkoxy, aryloxy, azido, cyano or alkylthio, $R^4$, $R^5$, $R^6$ and $R^7$ each, independently, is hydrogen or alkyl or, when $R^1$ is carboxy or alkoxycarbonyl and n stands for 1, $R^4$ and $R^6$ taken together can be a carbon-carbon bond or, when $R^2$ is carboxy or alkoxycarbonyl, $R^5$ and $R^7$ taken together can be a carbon-carbon bond, $R^8$ is halogen, alkyl, haloalkyl or alkoxy and $R^9$ is hydrogen, halogen, alkyl or alkoxy, and pharmaceutically acceptable salts of the compounds of formula I in which one of $R^1$ and $R^2$ is carboxy and the other is hydrogen with bases, can be used as medicaments for the treatment of rheumatoid arthritis, inflammatory respiratory diseases, inflammatory bowel disease, shock and inflammation associated with ischemia. The compounds of formula I can be prepared according to methods hereinafter described.

20 Claims, No Drawings

OTHER PUBLICATIONS of interleukin 1 beta production in organ culture of colonic biopsy specimens from patients with inflammatory bowel disease, Gut, 1991, 32, 50-54.

Ligumsky, et al., Role of interleukin 1 in inflammatory bowel disease-enhanced production during active disease, Gut, 1990, 31, 686-689.

Mahida, et al., Enhanced production of interleukin 1 beta by mononuclear cells isolated from mucosa with active ulcerative colitis of Crohn's disease, Gut, 1989, 30, 835-838.

Cominelli, et al., Interleukin-1 in the pathogenesis of and protection from inflammatory bowel disease, Biotherapy 1: 369-375, 1989.

Cominelli, Interleukin 1 (IL-1) Gene Expression, Synthesis, and Effect of Specific IL-1 Receptor Blockade in Rabbit Immune Complex Colitis, J. Clin. Invest., vol. 86, Sep. 1990, 972-980.

Dayer J-M et al., Production of Collagenase and Prostaglandins by Isolated Adherent Rheumatoid Synovial Cells, Proc. Nat. Acad. Sci. U.S.A., 73, 945 (1976).

Mizel, S. B. et al., Proc. Nat. Acad. Sci. U.S.A. 78, 2474, (1981).

Eastgate, J. A. et al., Lancet, 706, (1988).

Jandl, R. C. et al., Clin. Immunol. Immunopathol., 45, 384, (1987).

Bender, P. E. & Lee, J. C., Ann. Rep. Med. Chem., 25, 185 (1989).

Neuman, R. G. et al., Inhibition of Prostaglandin Biosynthesis by Etodolac, Agents and Actions, 21, 160 (1987).

SUBSTITUTED ISOXAZOLE DERIVATIVES

BRIEF SUMMARY OF THE INVENTION

The invention relates to heterocyclic compounds. More particularly, the invention relates to heterocyclic compounds of the formula

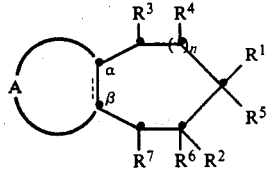

wherein A taken together with the two carbon atoms denoted as α and β are a group of the formula

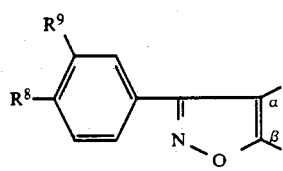

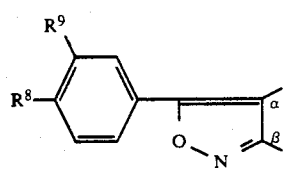

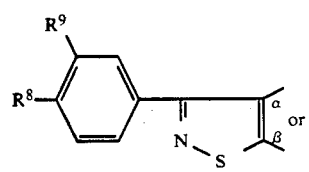

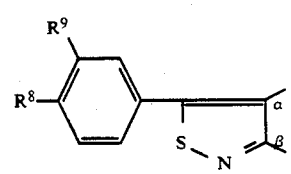

and the dotted line is the double bond present in formulas (i) and (iii); and wherein n is zero, 1,2 or 3, one of $R^1$ and $R^2$ is carboxy or alkoxycarbonyl and the other is hydrogen, $R^3$ is hydrogen, alkyl, alkoxy, aryloxy, azido, cyano or alkylthio, $R^4$, $R^5$, $R^6$ and $R^7$ each, independently, is hydrogen or alkyl or, when $R^1$ is carboxy or alkoxycarbonyl and n is 1, $R^4$ and $R^6$ taken together can be a carbon-carbon bond or when $R^2$ is carboxy or alkoxycarbonyl, $R^5$ and $R^7$ taken together can be a carbon-carbon bond, $R^8$ is halogen alkyl, haloalkyl or alkoxy and $R^9$ is hydrogen, halogen, alkyl or alkoxy, and pharmaceutically acceptable salts of the compounds of formula I in which one of $R^1$ and $R^2$ is carboxy and the other is hydrogen with bases.

In another aspect, the invention relates to compositions and methods comprising the compounds of formula I. In yet another aspect the invention relates to intermediates.

DETAILED DESCRIPTION OF THE INVENTION

The invention relates to heterocyclic compounds. More particularly, the invention relates to heterocyclic compounds of the formula

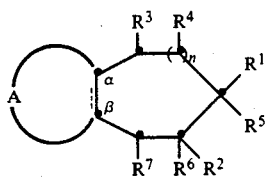

wherein A taken together with the two carbon atoms denoted as α and β is a group of the formula

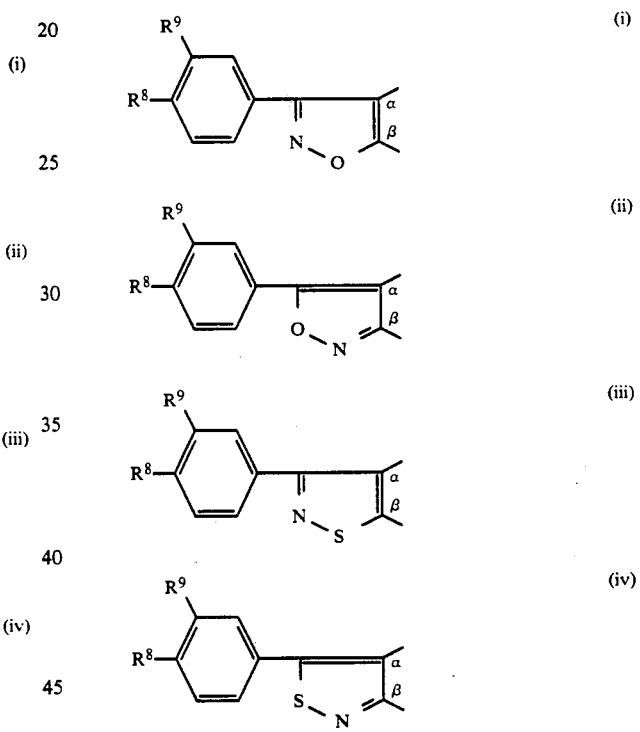

and the dotted line is the double bond present in formulas (i) and (iii); and wherein n is zero, 1,2 or 3, one of $R^1$ and $R^2$ is carboxy or alkoxycarbonyl and the other is hydrogen, $R^3$ is hydrogen, alkyl, alkoxy, aryloxy, azido, cyano or alkylthio, $R^4$, $R^5$, $R^6$ and $R^7$ each, independently, is hydrogen or alkyl or, when $R^1$ is carboxy or alkoxycarbonyl and n is 1, $R^4$ and $R^6$ taken together can be a carbon-carbon bond or, when $R^2$ is carboxy or alkoxycarbonyl, $R^5$ and $R^7$ taken together can be a carbon-carbon bond, $R^8$ is halogen, alkyl, haloalkyl or alkoxy and $R^9$ is hydrogen, halogen, alkyl or alkoxy, and pharmaceutically acceptable salts of the compounds of formula I in which one of $R^1$ and $R^2$ is carboxy and the other is hydrogen with bases.

The compounds and salts of formula I posses valuable pharmological properties and may be used in the treatment of illnesses. In particular said compounds are effective as modulators of cytokine-induced inflammatory conditions such as rheumatoid arthritis, inflammatory respiratory diseases, inflammatory bowel disease, shock and inflammation associated with ischemia, and can be used in the treatment of such conditions.

Objects of the invention are the compounds of formula I and their aforementioned salts including their use as therapeutically active substances, a process for the preparation of said compounds and salts, intermediates used in said process, medicaments containing a compound of formula I or an aforementioned salt thereof and the use of a compound of formula I or an aforementioned salt thereof in the treatment of illness and for the preparation of a medicament for the treatment of rheumatoid arthritis, inflammatory respiratory diseases, inflammatory bowel disease, shock and inflammation associated with ischemia.

As used herein, "alkyl" shall mean a straight-chain or branched chain alkyl group containing from 1 to 6, preferably from 1 to 4, carbon atoms such as methyl, ethyl, propyl, isopropyl, butyl, sec.butyl, tert.butyl, pentyl, hexyl and the like. The term "haloalkyl" shall mean an alkyl group as defined above in which one or more hydrogen atoms is or are replaced by halogen that is, fluorine, chlorine, bromine or iodine, examples of such haloalkyl groups are chloromethyl, trifluoromethyl and the like. The term "alkoxy", alone or in combination as in "alkoxycarbonyl", shall mean a straight-chain alkoxy group containing from 1 to 6, preferably from 1 to 4, carbon atoms, examples of alkoxy groups are methoxy, ethoxy, propoxy, isopropoxy, butoxy, tert.butoxy and the like and examples of alkoxycarbonyl groups are methoxycarbonyl, ethoxycarbonyl and the like. The term "alkylthio" shall mean a straight-chain or branched-chain alkylthio group containing from 1 to 6, preferably from 1 to 4, carbon atoms such as methylthio, ethylthio and the like. The term "aryloxy" shall mean a phenoxy or naphthyloxy group which is optionally substituted by one or more substituents selected from halogen, alkyl and alkoxy, examples of such aryloxy groups are phenoxy, 2-naphthyloxy, 4-chlorophenoxy, p-tolyloxy and the like.

The compounds of formula I contain at least one asymmetric carbon atom and, depending on the number of such carbon atoms present, can occur as optically active enantiomers, as diastereoisomers or as mixtures, for example, as racemic mixtures. Furthermore, depending on the significance of $R^3$, $R^4$, $R^5$, $R^6$ and $R^7$, the compounds can occur as cis and trans isomers or mixtures thereof. The invention includes within its scope all of these forms.

In formula I above, A taken together with the two carbon atoms denoted as $\alpha$ and $\beta$ preferably is a group of formula (i). The symbol n preferably stands for zero or 1. Preferably, one of $R^1$ and $R^2$ is carboxy and the other is hydrogen. $R^3$ preferably is hydrogen, alkyl, alkoxy or alkylthio, especially hydrogen, methyl, methoxy or methylthio. Preferably, $R^4$, $R^5$, $R^6$ and $R^7$ each are hydrogen or, when $R^2$ is carboxy, $R^5$ and $R^7$ taken together are a carbon-carbon bond and $R^6$ is hydrogen or alkyl, especially ethyl. Preferably, $R^8$ is halogen, especially chlorine, or alkoxy, especially methoxy, and $R^9$ is hydrogen.

Especially preferred compounds of formula I are:
(+)-3-(4-Chlorophenyl)-5,6,7,8-tetrahydro-4H-cyclohept[d]isoxazole-6-carboxylic acid,
3-(4-chlorophenyl)-5,6,7,8-tetrahydro-4H-cyclohept[d]isoxazole-7-carboxylic acid,
endo-3-(4-chlorophenyl)-5,5a,6,6a-tetrahydro-4H-cyclopropa[g]-1,2-benzisoxazole-6-carboxylic acid.

trans-3-(4-chlorophenyl)-5,6,7,8-tetrahydro-4-methoxy-4H-cyclohept[d]isoxazole-7-carboxylic acid.
trans-3-(4-chlorophenyl)-5,6,7,8-tetrahydro-4-methyl-4H-cyclohept[d]isoaxazole-7-carboxylic acid, and
endo-3-(4-chlorophenyl)-6-ethyl-5,5a,6,6a-tetrahydro-4H-cyclopropa[g]-1,2-benzisoxazole-6-carboxylic acid.

According to the process provided by the invention, the compounds of formula I hereinbefore and pharmaceutically acceptable salts of the compounds of formula I in which one of $R^1$ and $R^2$ is carboxy and the other is hydrogen with bases are prepared by (a) for the preparation of a compound of formula I in which A taken together with the two carbon atoms denoted as $\alpha$ and $\beta$ is a group of formula (i) and $R^3$ is hydrogen or alkyl, treating a compound of the formula

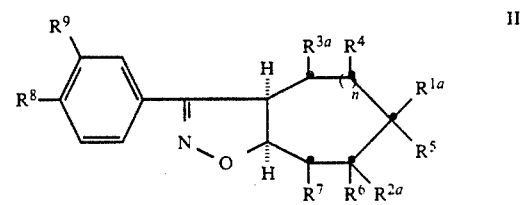

wherein one of $R^{1a}$ and $R^{2a}$ is alkoxycarbonyl and the other is hydrogen, $R^{3a}$ is hydrogen or alkyl and $R^4$, $R^5$, $R^6$, $R^7$, $R^8$, $R^9$ and n have the significance given earlier, with pyridinium bromide perbromide or chromic acid, or (b) for the preparation of a compound of formula I in which A taken together with the two carbon atoms denoted as $\alpha$ and $\beta$ is a group of formula (i) and $R^3$ is hydrogen or alkyl, treating a compound of the formula

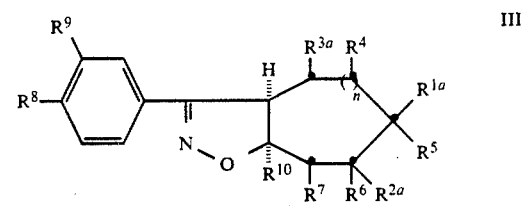

wherein $R^{1a}$, $R^{2a}$, $R^{3a}$, $R^4$, $R^5$, $R^6$, $R^7$, $R^8$, $R^9$ and n have the significance given earlier and $R^{10}$ is pyrrolidino or trialkylsilyloxy, with an acid, or (c) for the preparation of a compound of formula I in which A taken together with the two carbon atoms denoted as $\alpha$ and $\beta$ is a group of the formula (i), $R^1$ is carboxy, $R^2$ is hydrogen, $R^5$ is hydrogen and $R^6$ is hydrogen or alkyl or $R^1$ is hydrogen, $R^2$ is carboxy, $R^5$ is hydrogen or alkyl and $R^6$ is hydrogen, and $R^3$ is hydrogen or alkyl, decarboxylating a compound of the formula

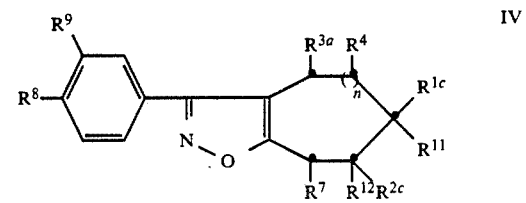

wherein $R^{3a}$, $R^4$, $R^7$, $R^8$, $R^9$ and n have the significance given earlier, $R^{1c}$ and $R^{11}$ both are carboxy, $R^{2c}$ is hydrogen and $R^{12}$ is hydrogen or alkyl or $R^{2c}$ and $R^{12}$ both are carboxy, $R^{1c}$ is hydrogen and $R^{11}$ is hydrogen or alkyl, (d) for the preparation of a compound of formula I in which A taken together with the two carbon atoms denoted as α and β is a group of formula (i), one of $R^1$ and $R^2$ is alkoxycarbonyl and the other is hydrogen and $R^3$ is hydrogen or alkyl, subjecting a compound of the formula

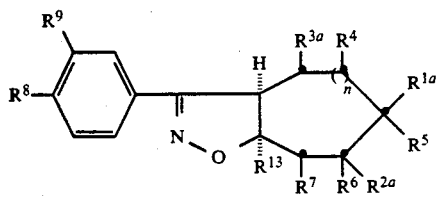

V wherein $R^{1a}$, $R^{2a}$, $R^{3a}$, $R^4$, $R^5$, $R^6$, $R^7$, $R^8$, $R^9$ and n have the significance given earlier and $R^{13}$ is N-oxido-1-pyrrolidinyl, to thermolysis, or (e) for the preparation of a compound of formula I in which A taken together with the two carbon atoms denoted as α and β is a group of formula (i), one of $R^1$ and $R^2$ is carboxy and the other is hydrogen and $R^3$ is hydrogen or alkyl, treating a compound of the formula

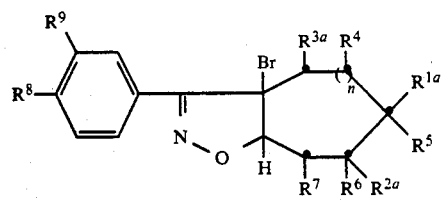

VI wherein $R^{1a}$, $R^{2a}$, $R^{3a}$, $R^4$, $R^5$, $R^6$, $R^7$, $R^8$, $R^9$ and n have the significance given earlier, with an alkali metal hydroxide, or (f) for the preparation of a compound of formula I in which A taken together with the two carbon atoms denoted as α and β is a group of formula (ii), one of $R^1$ and $R^2$ is alkoxycarbonyl and the other is hydrogen and $R^3$ is hydrogen or alkyl, reacting a compound of the formula

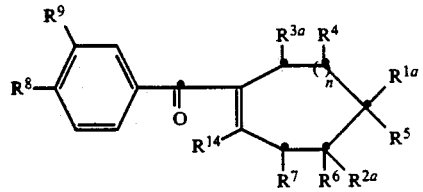

VII wherein $R^{1a}$, $R^{2a}$, $R^{3a}$, $R^4$, $R^5$, $R^6$, $R^7$, $R^8$, $R^9$ and n have the significance given earlier and $R^{14}$ is morpholino, with hydroxylamine, or (g) for the preparation of a compound of formula I in which A taken together with the two carbon atoms denoted as α and β is a group of formula (iii) or (iv), one of $R^1$ and $R^2$ is alkoxycarbonyl and the other is hydrogen and $R^3$ is hydrogen or alkyl, reacting a compound of the formula

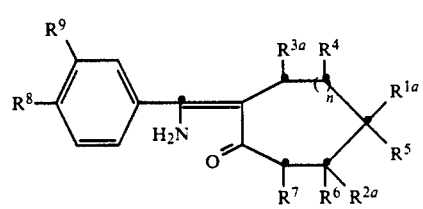

VIII

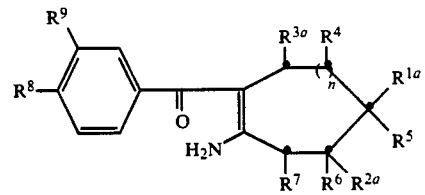

IX wherein $R^{1a}$, $R^{2a}$, $R^{3a}$, $R^4$, $R^5$, $R^6$, $R^7$, $R^8$, $R^9$ and n have the significance given earlier, with phosphorus pentasulfide, or (h) for the preparation of a compound of formula I in which $R^5$, $R^6$ and $R^7$ is alkyl, introducing an alkyl group into a corresponding compound of formula I in which $R^5$, $R^6$ or $R^7$ is hydrogen, or (i) for the preparation of a compound of formula I in which one of $R^1$ and $R^2$ is carboxy and the other is hydrogen and $R^3$ is alkoxy, subjecting a compound of the formula

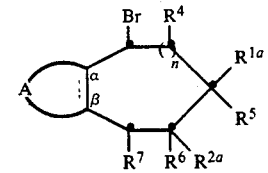

X wherein A, $R^{1a}$, $R^{2a}$, $R^4$, $R^5$, $R^6$, $R^7$ and n have the significance given earlier, to an alkanolysis, or (j) for the preparation of a compound of formula I in which one of $R^1$ and $R^2$ is alkoxycarbonyl and the other is hydrogen and $R^3$ is alkoxy or aryloxy, reacting a compound of formula X hereinbefore with a compound of the formula $R^{3b}$—OM    XI wherein $R^{3b}$ is alkyl or aryl and M is an alkali metal, or (k) for the preparation of a compound of formula I in which one of $R^1$ and $R^2$ is alkoxycarbonyl and the other is hydrogen and $R^3$ is azido, reacting a compound of formula X hereinbefore with an alkali metal azide, or (l) for the preparation of a compound of formula I in which one of $R^1$ and $R^2$ is alkoxycarbonyl and the other is hydrogen and $R^3$ is methyl, catalytically hydrogenating a compound of the formula

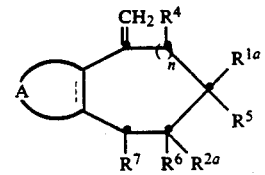

XII wherein A, $R^{1a}$, $R^{2a}$, $R^4$, $R^5$, $R^6$, $R^7$ and n have the significance given earlier, (m) for the preparation of a compound of formula I in which one of $R^1$ and $R^2$ is alkoxycarbonyl and the other is hydrogen and $R^3$ is cyano, reacting a compound of formula X hereinbefore with an alkali metal cyanide, or (n) for the preparation of a compound of formula I in which one of $R^1$ and $R^2$ is alkoxycarbonyl and the other is hydrogen and $R^3$ is alkylthio, reacting a compound of formula X hereinbefore with an alkali metal alkanethiolate, or (o) for the preparation of a compound of formula I in which one of $R^1$ and $R^2$ is carboxy and the other is hydrogen, hydrolyzing a compound of formula I in which one of $R^1$ and $R^2$ is alkoxycarbonyl and the other is hydrogen, and (p) if desired, converting a compound of formula I obtained in which one of $R^1$ and $R^2$ is carboxy and the other is hydrogen into a pharmaceutically acceptable salt with a base.

The treatment of a compound of formula II with pyridinium bromide perbromide in accordance with process embodiment (a) is conveniently carried out in the presence of an alkanoic acid, for example, acetic acid, and at an elevated temperature, especially at or near the boiling point of the reaction mixture. This treatment with pyridinium bromide perbromide yields a carboxylic acid of formula I, that is, where one of $R^1$ and $R^2$ is carboxy and the other is hydrogen. The treatment of a compound of formula II with chromic acid, also in accordance with embodiment (a) of the process, is conveniently carried out in the presence of an alkanoic acid, for example, acetic acid, which preferably contains a trace of sulfuric acid, and at an elevated temperature, suitably at or near the boiling point of the reaction mixture. This treatment with chromic acid yields a carboxylic acid ester of formula I, that is, where one of $R^1$ and $R^2$ is alkoxycarbonyl and the other is hydrogen.

The treatment of a compound of formula III with an acid in accordance with process embodiment (b) is conveniently carried out using a mineral acid such as a hydrohalic acid, for example, hydrochloric acid, hydrobromic acid and the like, sulfuric acid, optionally in admixture with an alkanoic acid such as acetic acid, and the like, whereby there is obtained a carboxylic acid of formula I, that is, where one of $R^1$ and $R^2$ is carboxy and the other is hydrogen. Alternatively, an alkanolic hydrogen halide, for example, methanolic hydrogen chloride, or the like, can be used and in this case there is obtained a carboxylic acid ester of formula I, that is, where one of $R^1$ and $R^2$ is alkoxycarbonyl and the other is hydrogen. This treatment is suitably carried out at an elevate temperature, preferable at a temperature between about 50° C. and the reflux temperature of the reaction mixture.

The decarboxylation of a compound of formula IV in accordance with process embodiment (c) can be carried out by heating the compound of formula IV at an elevated temperature, for example, about 180°-220° C. until the evolution of carbon dioxide has ceased.

The thermolysis of a compound of formula V in accordance with process embodiment (d) is expediently carried out in the absence of a solvent or diluent and at a temperature between about 100° C. and about 160° C.

The treatment of a compound of formula VI with an alkali metal hydroxide in accordance with process embodiment (e) is conveniently carried out in the presence of a water-miscrible organic solvent which is inert under the reaction conditions, for example, an alkanol such as methanol, ethanol or the like, and at a temperature between about 15° C. and about 30° C., preferably at about room temperature.

The reaction of a compound of formula VII with hydroxylamine in accordance with process embodiment (f) is expediently carried out using hydroxylamine in the form of an acid addition salt, for example, as a hydrohalide such as hydroxylamine hydrochloride. Conveniently, the reaction is carried out in an organic solvent which is inert under the reaction conditions, for example, an alkanol such as ethanol, or the like, and in the presence of a tertiary organic base such as pyridine, or the like. This reaction is expediently carried out at an elevated temperature, preferably at or near the reflux temperature of the reaction mixture.

The reaction of a compound of formula VIII or IX with phosphorus pentasulfide in accordance with process embodiment (g) is conveniently carried out in an organic solvent which is inert under the reaction conditions, for example, an aromatic hydrocarbon such as benzene, toluene, o-xylene or the like, under anhydrous conditions and in the presence of 2,3,5,6-tetrachloro-p-benzoquinone. The reaction is expediently carried out an elevated temperature, preferably at or near the reflux temperature of the reaction mixture.

The introduction of an alkyl group into a compound of formula I in which $R^5$, $R^6$ or $R^7$ is hydrogen in accordance with embodiment (h) of the process can be carried out in a known manner. For example, a compound of formula I in which $R^5$, $R^6$ or $R^7$ is hydrogen can be reacted firstly with lithium diisopropylamide in an organic solvent which is inert under the reaction conditions, for example, a cyclic ether such as tetrahydrofuran or the like, and at a low temperature, for example, at about $-70°$ C., and the reaction product can be reacted in situ with an alkyl halide, preferably an alkyl iodide such as methyl iodide or the like, conveniently in the same organic solvent in which the initial reaction has been carried out, and at about $-70°$ C. to about 30° C., preferably at about room temperature.

The alkanolysis of a compound of formula X in accordance with process embodiment (i) can be carried out according to known methods. For example, a compound of formula X in an appropriate alkanol such as methanol, ethanol or the like, can be treated with an aqueous alkali metal hydroxide solution such as aqueous sodium hydroxide solution or aqueous potassium hydroxide solution. This treatment is expediently carried out at a temperature between about 15° C. and about 30° C., preferably at about room temperature.

The reaction of a compound of formula X with a compound of formula XI in accordance with process embodiment (j) can also be carried out in a known manner. Conveniently, the reaction is carried out in an organic solvent which is inert under the reaction conditions, for example, an aliphatic ether such as dimethoxyethane or the like, and at a temperature between about 15° C. and about 30° C., preferably at about room temperature.

The reaction of a compound of formula X with an alkali metal azide in accordance with process embodiment (k) can also be carried out in a known manner. Conveniently, the reaction is carried out in an organic solvent which is inert under the reaction conditions, for example, an aliphatic ether such as dimethoxyethane or the like and at a temperature between about 15° C. and about 30° C., preferably at about room temperature. Sodium azide is the preferred alkali metal azide.

The catalytic hydrogenation of a compound of formula XII in accordance with process embodiment (l) can be carried out in a known manner. Conveniently, the catalytic hydrogenation is carried out using a platinum catalyst such as platinum-on-carbon and in an acidic medium such as an alkanoic acid for example, glacial acetic acid. The catalytic hydrogenation is preferably carried out at room temperature an under atmospheric pressure.

The reaction of a compound of formula X with an alkali metal cyanide in accordance with process embodiment (m) can be carried out in a known manner. Conveniently, the reaction is carried out in an organic solvent which is inert under the reaction conditions, preferably dimethylformamide or the like, and at a temperature between about 15° C. and 30° C., preferably at about room temperature. Sodium cyanide is the preferred alkali metal cyanide.

The reaction of a compound of formula X with an alkali metal alkanethiolate in accordance with process embodiment (n) can be carried out in a known manner. Suitably, the reaction is carried out in an organic solvent which is inert under the reaction conditions, preferably dimethylformamide or the like, and at a temperature between about 15° C. and about 30° C., preferably at about room temperature. It is preferred to use a sodium alkanethiolate, especially sodium methanethiolate.

The hydrolysis of a compound of formula I in which one of $R^1$ and $R^2$ is alkoxycarbonyl and the other is hydrogen in accordance with embodiment (o) of the process can be carried out according to known methods. Thus, for example, the hydrolysis can be carried out using a base such as an alkali metal hydroxide, for example sodium hydroxide or potassium hydroxide, conveniently in a water-miscrible organic solvent which is inert under the reaction conditions, for example, an alkanol such as methanol, ethanol or the like, and at an elevated temperature, for example, a temperature of or near the reflux temperature of the reaction mixture. Alternatively, the hydrolysis can be carried out by treatment with an acid such as sulfuric acid, conveniently at a temperature between about 15° C. and about 30° C., preferably at about room temperature.

The compounds of formula I in which one of $R^1$ and $R^2$ is carboxy and the other is hydrogen can be converted into pharmaceutically acceptable salts with bases in accordance with process embodiment (P). Examples of such salts are alkali metal salts, for example sodium and potassium salts, alkaline earth metal salts for example, calcium and magnesium salts, ammonium salts and salts with organic amines, for example, dicyclohexylamine salts. The salts can be prepared by treating a compound of formula I in which one of $R^1$ and $R^2$ is carboxy and the other is hydrogen with an appropriate base according to known procedures.

The compounds of formula II which are used as starting materials in process embodiment (a) are also an object of the invention. They can be prepared by reacting a compound of the formula

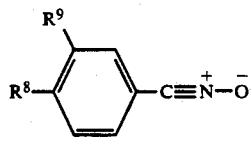

XIII wherein $R^8$ and $R^9$ have the significance given earlier, with a compound of the formula

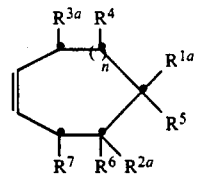

XIV wherein $R^{1a}$, $R^{2a}$, $R^{3a}$, $R^{4a}$, $R^5$, $R^6$, $R^7$ and n have the significance given earlier.

Conveniently, the compound of formula XIII is prepared in situ from the corresponding benzaldehyde oxime and an alkali metal hypochlorite and the reaction is carried out in a two-phase system comprising water and organic solvent which is inert under the reaction conditions, for example an alkyl alkanoate such as ethyl acetate, and in the presence of a phase-transfer catalyst such as tetrabutylammonium bromide. Suitably, the reaction is carried out at a temperature between about 15° C. and about 30° C., preferably at about room temperature.

The compounds of formula III which are used as starting materials in process embodiment (b) also form an object of the invention. They can be prepared by reacting a compound of formula XIII above a compound of the formula

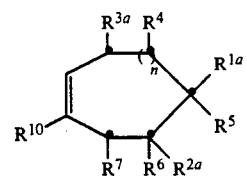

XV wherein $R^{1a}$, $R^{2a}$, $R^{3a}$, $R^4$, $R^5$, $R^6$, $R^7$, $R^{10}$ and n have the significance given earlier.

This reaction is expediently carried out in an organic solvent such as an ether, for example, diethyl ether or the like or a halogenated aliphatic hydrocarbon, for example, dichloromethane or the like and at a temperature between about 15° C. and about 30° C., preferably at about room temperature.

The compounds of formula IV which are used as starting materials in process embodiment (c) also form an object of the invention. They can be prepared by reacting a compound of the formula XIII above with a compound of the formula

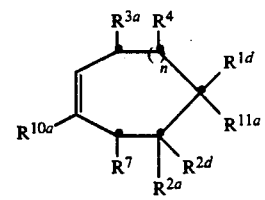

XVI wherein $R^{3a}$, $R^4$, $R^7$, $R^{11}$, $R^{12}$, and n have the significance given earlier; $R^{1d}$, and $R^{11a}$ both are alkoxycarbonyl, $R^{2d}$ is hydrogen and $R^{12a}$ is hydrogen or alkyl or $R^{2d}$ and $R^{12a}$ both are alkoxycarbonyl, $R^{1d}$ is hydrogen and $R^{11a}$ is hydrogen or alkyl, and $R^{10a}$ is pyrrolidino, treating the resulting compound of the formula

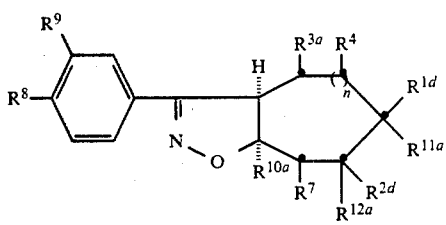

XVII wherein $R^{1d}$, $R^{2d}$, $R^{3a}$, $R^4$, $R^7$, $R^8$, $R^9$, $R^{10a}$, $R^{11a}$, $R^{12a}$ and n have the significance given earlier, with an acid and hydrolyzing the resulting compound of the formula

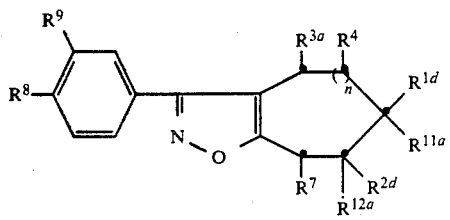

XVIII wherein $R^{1d}$, $R^{2d}$, $R^{3a}$, $R^4$, $R^7$, $R^8$, $R^9$, $R^{11a}$, $R^{12a}$ and n have the significance given earlier, The reaction of a compound of formula XIII with a compound of formula XVI can be carried out in a manner analogous to that described earlier in connection with the reaction of a compound of formula XIII with a compound of formula XV. The treatment of a compound of formula XVII with an acid and the subsequent hydrolysis of a compound of formula XVIII can be carried out in an analogous manner to that described in connection with embodiments (b) and (o), respectively, of the process in accordance with the invention.

The compounds of formula V which are used as starting materials in process embodiment (d) also form an object of the invention. They can be prepared by N-oxidizing a compound of formula III above in which $R^{10}$ is pyrrolidino. The N-oxidation can be carried out, for example, using a peracid such as m-chloroperbenzoic acid in an organic solvent which is inert under the reaction conditions, for example, a halogenated hydrocarbon such as chloroform, conveniently a temperature of about 15° C. to about 30° C., preferably at about room temperature.

The compounds of formula VI which are used as starting materials in process embodiment (e) also form an object of the invention. They can be prepared by reacting a compound of formula II hereinbefore with N-bromosuccinimide. This reaction is expediently carried out in the presence of a catalytic amount of dibenzoyl peroxide in an organic solvent which is inert under the reaction conditions, for example, a halogenated hydrocarbon such as carbon tetrachloride. Conveniently, this reaction is carried out at an elevated temperature, preferably at or near the reflux temperature of the reaction mixture.

The compounds of formula VII which are used as starting materials in process embodiment (f) also form an object of the invention. They can be prepared by reacting a compound of the formula

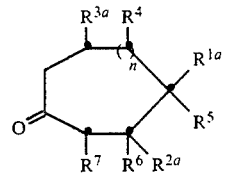

XIX wherein $R^{1a}$, $R^{2a}$, $R^{3a}$, $R^4$, $R^5$, $R^6$, $R^7$ and n have the significance given earlier, with morpholine and reacting the resulting compound of the formula

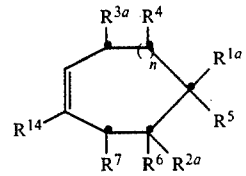

XX wherein $R^{1a}$, $R^{2a}$, $R^{3a}$, $R^4$, $R^5$, $R^6$, $R^7$, $R^{14}$ and n have the significance given earlier, with a compound of the formula

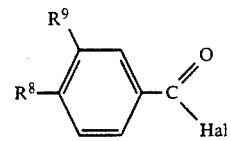

XXI wherein $R^8$ and $R^9$ have the significance given earlier and Hal stands for a halogen atom, preferably a chlorine atom.

The reaction of a compound of formula XIX with morpholine can be carried out in a known manner; for example, in an organic solvent which is inert under the reaction conditions, such as an aromatic hydrocarbon, for example, benzene, toluene, o-xylene, or the like, and in the presence of a catalytic amount of p-toluenesulfonic acid at an elevated temperature, preferably at the reflux temperature of the reaction mixture. The resulting compound of formula XX is preferably not isolated, but is reacted directly in situ with a compound of formula XXI, conveniently in the presence of a teritary organic base such as trialkylamine, for example, triethylamine, or the like, and at a temperature between about 20° C. and about 60° C.

The compounds of formula VIII and IX which are used as starting materials in process embodiment (g) also form an object of the invention. They can be prepared by hydrogenolyzing a compound of formula I in which A together with two carbon atoms denoted as α and β is a group of formula (i) or, respectively, formula (ii), one of $R^1$ and $R^2$ is alkoxycarbonyl and the other is hydrogen and $R^3$ is hydrogen or alkyl. This hydrogenolysis is conveniently effected in the presence of Raneynickel and in a conventional organic solvent such as an alkanol, for example, methanol, or the like. The hydrogenolysis is expediently carried out at about room temperature and at atmospheric pressure or at an elevated pressure.

The compounds of formula X which are used as starting materials in process embodiment (i) also form an object of the present invention. They can be prepared by reacting a compound of formula I in which one of $R^1$ and $R^2$ is alkoxycarbonyl and the other is hydrogen and $R^3$ is hydrogen with N-bromosuccinimide. Conveniently this reaction is carried out in the presence of a catalytic amount of dibenzoyl peroxide, in an organic solvent which is inert under the reaction conditions, for example, a halogenated aliphatic hydrocarbon such as carbon tetrachloride, and at an elevated temperature, for example, or near the reflux temperature of the reaction mixture.

The compounds of formula XII which are used as starting materials in process embodiment (l) also form an object of the invention. They can be prepared by treating a compound of formula X hereinbefore with water, oxidizing the resulting compound of the formula

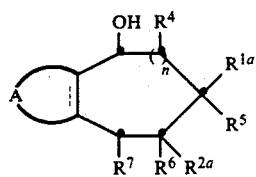

XXII wherein A, $R^{1a}$, $R^{2a}$, $R^4$, $R^5$, $R^6$, $R^7$ and n have the significance given earlier, and reacting the resulting compound of the formula

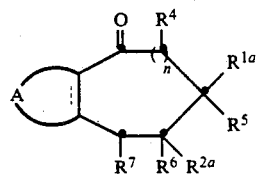

XXIII wherein A, $R^{1a}$, $R^{2a}$, $R^4$, $R^5$, $R^6$, $R^7$ and n have the significance given earlier, with a methyltriarylphosphonium halide in a Wittig reaction.

The treatment of a compound of formula X with water is expediently carried out in a water-miscible organic solvent which is inert under the reaction conditions, for example, a cyclic ether such as dioxane or the like, and at about 15° C. to about 30° C., preferably at about room temperature. The oxidation of a compound of formula XXII can be carried out according to known methods, suitably using Jones' reagent in the presence of an organic solvent which is inert under the reaction conditions, for example, a ketone such as acetone or the like, and at a temperature between about 15° C. and about 30° C., preferably at about room temperature. The subsequent reaction of a compound of formula XXIII with a methyltriarylphosphonium halide, preferably methyltriphenylphosphonium bromide, can be carried out under conditions which are known for Wittig reactions.

The remaining materials which are used in the process in accordance with the invention as well as the compounds which are used in the preparation of the starting materials are known substances or analogues of known substances which can be prepared in analogy to the known substances.

As mentioned earlier, the compounds of formula 1 above and pharmaceutically acceptable salts of said compounds in which one of $R^1$ and $R^2$ is carboxy and the other is hydrogen with bases possess valuable pharmacological properties.

The activity of the compounds of formula I and salts thereof can be determined using the following test:

IL-1-dependent PGE 2 inhibition test:

Human rheumatoid synovial cell lines, prepared by the enzymatic dissociation of fresh rheumatoid tissue, were maintained by culture in Dulbecco's modified Eagle medium containing 25 mM HEPES, 10% foetal calf serum, 100 units of penicillin per ml and 100 μg of streptomycin per ml (culture medium). Standard incubation conditions were 37° C. in a water-saturated atmosphere containing 95% air and 5% $CO_2$.

Semi-confluent cultures at the third to eighteenth passage were detached by trypsin treatment and resuspended in culture medium at $1 \times 10^{-5}$/ml. The cell suspension was distributed to 200 μl aliquots into the wells of a 96-well microtitration plate and incubated for 18 hours at 37° C. to allow adhesion of the cells.

Test substances were dissolved in equimolar sodium hydroxide solution and double-dilution series were prepared in sterile water. If the test substances is a compound of formula I in which one of $R^1$ and $R^2$ is alkoxycarbonyl and the other hydrogen, it is treated with hog liver esterase prior to carrying out the test. The medium was aspirated from the microcultures of the synovial cells. 170 μl of culture medium were added and the cultures were treated with 20 μl of test substances and then 10 μl of recombinant human IL-1 alpha culture medium to give a final concentration of 0.1 ng/ml. All treatments were carried out in quadruplet. After incubation for 7 hours, samples of the culture media were removed and stored at $-20°$ C. prior to assay for $PGE_2$. The $PGE_2$ content was determined using a $[^{125}I]RIA$ kit obtained from NEN Products.

$PGE_2$ concentration detected in unstimulated controls were subtracted from values determined in all stimulated cultures and results were transformed to percent of IL-1-stimulated control $PGE_2$ values. $IC_{50}$ values were determined by interpolation as those concentrations reducing $PGE_2$ release to 50% of IL-1-stimulated control values.

The results obtained in the foregoing test with representative compounds of formula I are compiled in the following Table:

TABLE

| Compound | $IC_{50}$ |
|---|---|
| A | 2 μM |
| B | 15 μM |
| C | 0.5 μM |
| D | 8 μM |
| E | 0.04 μM |
| F | 0.7 μM |

Compound A: (+)-3-(4-Chlorophenyl)-5,6,7,8-tetrahydro-4H-cyclohept[d]isoxazole-6-carboxylic acid, Compound B: 3-(4-Chlorophenyl)-5,6,7,8-tetrahydro-4H-cyclohept[d]isoxazole-7-carboxylic acid, Compound C: endo-3-(4-Chlorophenyl)-5,5a,6,6a-tetrahydro-4H-cyclopropa[g]-1,2-benzisoxazole-6-carboxylic acid.

Compound D: trans-3-(4-Chlorophenyl)-5,6,7,8-tetrahydro-4-methoxy-4H-cyclohept[d]isoxazole-7-carboxylic acid.

Compound E: trans-3-(4-Chlorophenyl)-5,6,7,8-tetrahydro-4-methyl-4H-cyclohept[d]isoaxazole-7-carboxylic acid.

Compound F: endo-3-(4-Chlorophenyl)-6-ethyl-5,5a,6,6a-tetrahydro-4H-cyclopropa[g]-1,2-benzisoxazole-6-carboxylic acid.

The compounds of formula I and the pharmaceutically acceptable salts of compounds of formula I in which one of $R^1$ and $R^2$ is carboxy and the other is hydrogen with bases can be used as medicaments, for example, in the form of pharmaceutical preparations. The pharmaceutical preparations can be administered orally, for example, in the form of tablets, coated tablets, dragees, hard and soft gelatine capsules, solutions, emulsions or suspension. However, the administration can also be carried out rectally, for example, in the form of suppositories, or parenterally, for example, in the form of injection solutions.

Medicaments containing a product in accordance with the invention and a therapeutically inert carrier are also an object of the present invention. Such medicaments can be prepared by bringing a product in accordance with the invention and, if desired, one or more other therapeutically valuable substances into a galenical administration form together with one or more therapeutically inert excipients.

For preparation of medicaments, compounds of formula I and salts thereof in accordance with the invention can be processed with pharmaceutically inert, inorganic or organic carriers. Lactose, maize starch or derivatives thereof, talc, stearic acid or its salts and the like can be used, for example, as such carriers for tablets, coated tablets, dragees and hard gelatine capsules. Suitable carriers for soft gelatin capsules are, for example, vegetable oils, waxes, fats, semi-solid and liquid polyols and the like. Depending on the nature of the active substance no carriers are, however, required in the case of soft gelatine capsules. Suitable carriers for the preparation of solutions and syrups are, for example, water, polyols, saccharose, invert sugar, glucose and the like. Suitable carriers for injection solutions are, for example, water, alcohols, polyols, glycerin, vegetable oils and the like. Suitable carriers for suppositories are, for example, natural hardened oils, waxes, fats, semi-liquid or liquid polyols and the like.

The medicaments can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances.

As mentioned earlier, the compounds of formula I and salts thereof in accordance with the invention can be used in the treatment of illnesses, especially in the treatment of rheumatoid arthritis, inflammatory respiratory diseases, inflammatory bowel disease, shock and inflammation associated with ischemia. The dosage can vary within wide limits and will of course, be fitted to the individual requirements in each particular case. In the case of oral administration a daily dosage in the range of about 10 mg to about 2000 mg should be appropriate.

The use of the products in accordance with the invention for the preparation of medicaments for the treatment of rheumatoid arthritis, inflammatory respiratory diseases, inflammatory bowel disease, shock and inflammation associated with ischemia is also an object of the invention.

The following Examples illustrate the invention in more detail:

EXAMPLE 1

A solution of 48.24 g (0.157 mol) of methyl 3-(4-chlorophenyl)-3a,5,6,7,8,8a-hexahydro-4H-cyclohept[d]isoxazole-6-carboxylate (mixture of two racemic diastereoisomers) and 57.61 g (0.18 mol) of pyridinium bromide perbromide in 630 ml of glacial acetic acid was heated at 88° C. for 7.5 hours while stirring. After 4.5 hours 30 ml of water were added. After removal of the acetic acid, the residue was partitioned between diethyl ether and 2N sodium carbonate solution. The aqueous-alkaline phase was separated and acidified with 2N. hydrochloric acid to give a thick brown oil which crystallized on standing. Recrystallization from ethyl acetate/hexane gave 36 g of racemic 3-(4-chlorophenyl)-5,6,7,8-tetrahydro-4H-cyclohept[d]isoxazole-6-carboxylic acid of melting point 143°-145° C.

3.30 g (0.02 mol) of l-ephedrine in 30 ml of ethyl acetate were added to 5.83 g (0.02 mol) of racemic 3-(4-chlorophenyl)-5,6,7,8-tetrahydro-4H-cyclohept[d]isoxazole-6-carboxylic acid in 50 ml of ethyl acetate while warming. The resulting crystalline salt was recrystallized five times from 100 ml of ethyl acetate each time to give 3 g of the pure (+) salt; $[\alpha]_D$ EtOH = +10.3°. Treatment of this salt with dilute sulfuric acid/diethyl ether gave 0.9 g of (+)-3-(4-chlorophenyl)-5,6,7,8-tetrahydro-4H-cyclohept[d]isoxazole-6-carboxylic acid of melting point 126°-128° C.; $[\alpha]_D$ EtOH = +42.7°.

The corresponding (−) acid was obtained from the above mother liquors in an analogous manner by resolution with d-ephedrine. The pure (−) salt had the resolution $[\alpha]_D = -9.7°$ and the (−)-3-(4-chlorophenyl)-5,6,7,8-tetrahydro-4H-cyclohept[d]isoxazole-6-carboxylic acid obtained therefrom had a melting point of 126°-130° C. and a rotation $[\alpha]_D$ EtOH = −41.9°.

The starting material was prepared as follows:

180 ml of 16.38% (w/v) aqueous solution of sodium hypochlorite were added slowly at 5° C. over a period of 6 hours while stirring well to a solution of 61.6 g (0.4 mol) of methyl cyclohept-4-enecarboxylate, 62.0 g (0.4 mol) of 4-chlorobenzaldehyde oxime and 0.5 g of tetrabutylammonium bromide in 800 ml of ethyl acetate. The mixture was held at 20° C. for 2 days. The mixture was then filtered and the organic phase was separated and dried over magnesium sulfate. The solvent was removed by evaporation and the residue was crystallized from diethyl ether/hexane to give 44.65 g of methyl 3-(4-chlorophenyl)-3a,5,6,7,8,8a-hexahydro-4H-cyclohept[d]isoxazole-6-carboxylate as a mixture of two diastereoisomers of melting point 150°-185° C. Isomer A has a melting point of 237°-239° C. and isomer B has a melting point of 162°-166° C.

EXAMPLE 2

5.3 g (0.053 mol) of chromium trioxide were added to a solution of 6.14 g (0.02 mol) of methyl 3-(4-chlorophenyl-3a,5,6,7,8,8a-hexahydro-4H-cyclohept[d]isoxazole-6-carboxylate (mixture of two diastereoisomers, prepared as described in the last paragraph of Example 1) in 110 ml of acetic acid and 0.5 ml of concentrated sulfuric acid. The mixture was heated to 90° C. for 40 minutes. Excess acetic acid was removed by evaporation, water and 2N sodium carbonate solution were added and the mixture was extracted with diethyl ether. Purification by column chromatography on silica gel using diethyl ether/hexane (1:1) for the elution gave 2.57 g or pure methyl 3-(4-chlorophenyl)-5,6,7,8-tetrahydro-4H-cyclohept[d]-isoxazole-6-carboxylate of melting point 70°-71° C.

EXAMPLE 3

2.5 of methyl 3-(4-chlorophenyl)-5,6,7,8-tetrahydro-4H-cyclohept[d]isoxazole-6-carboxylate in 20 ml of methanol were treated with 1.5 g of potassium hydroxide in 2 ml water at 20° C. for 16 hours. After removing the methanol by evaporation, the residue was taken up in water. The aqueous-alkaline solution was washed with diethyl ether, acidified with 2N hydrochloric acid and extracted with diethyl ether. After drying over magnesium sulfate and evaporation, there were obtained 1.8 g of 3-(4-chlorophenyl)-5,6,7,8-tetrahydro-4H-cyclohept[d]isoxazole-6-carboxylic acid of melting point 144°-145° C. after recrystallization from ethyl acetate/hexane.

EXAMPLE 4

20 g of methyl 3-(4-chlorophenyl)-3a,5,6,7,8,8a-hexahydro-8a-pyrrolidino-4H-cyclohept[d]isoxazole-7-carboxylate was heated under reflux in 500 ml of 10% methanolic hydrogen chloride solution for 10 hours. The methanol was removed by evaporation and dilute hydrochloric acid was added to the residue. The mixture was extracted with diethyl ether and the ethereal extract was dried over sodium sulfate and evaporated. There were obtained, after recrystallization from methanol, 8 g of methyl 3-(4-chlorophenyl)-5,6,7,8-tetrahydro-4H-cyclohept[d]isoxazole-7-carboxylate of melting point 108°-111° C.

The starting material was prepared as follows:

(A) A solution of 10.18 g (0.06 mol) of methyl 4-oxocycloheptanecarboxylate and 4.47 g (0.063 mol) of pyrrolidine in 50 ml of toluene containing 0.1 g of p-toluenesulfonic acid was heated under reflux for 3 hours in a Dean-Stark apparatus. The toluene was removed by distillation and the resulting enamine was dissolved in 50 ml of dry diethyl ether.

(B) An ethereal solution of 4-chlorophenyl nitrile oxide was prepared by slowly adding dropwise 6.66 g (0.066 mol) of triethylamine in 50 ml of dry diethyl ether while stirring at 5° C. to a solution of 12.54 g (0.066 mol) of 4-chlorobenzehecarboximidoyl-N-hydroxy-chloride in 50 ml of dry diethyl ether. After 0.5 hour, the solution was filtered.

(C) The solutions prepared according to paragraphs (A) and (B) were mixed and left to react for 16 hours. The mixture was filtered and the filtrate was extracted three times with 2N hydrochloric acid. The combined aqueous-acidic extracts were made alkaline by the addition of 2N solium carbonate solution. The resulting methyl 3-(4-chlorophenyl)-3a,5,6,7,8,8a-hexahydro-8a-pyrrolidino-4H-cyclohept[d]isoxazole-7-carboxylate was taken up in diethyl ether and the solution was dried over sodium sulfate and evaporated to give 20 g of a yellow oil; MS m/e 377 (M+H)+.

EXAMPLE 5

2,48 g of methyl 3-(4-chlorophenyl)-5,6,7,8-tetrahydro-4H-cyclohept[d]isoxazole-7-carboxylate were treated with 0.8 g of potassium hydroxide in 2 ml of water and 50 ml of methanol at 20° C. Methanol was removed from the mixture by evaporation and the residue was taken up in water. After washing with diethyl ether, the aqueous alkaline solution was acidified with 2N hydrochloric acid and extracted with diethyl ether. The ethereal extract was dried over magnesium sulfate and evaporated to give 1.9 g of 3-(4-chlorophenyl)-5,6,7,8-tetrahydro-4H-cyclohept[d]-isoxazole-7-carboxylic acid of melting point 215°-217° C. (from methanol).

EXAMPLE 6

5 g of methyl 3-(4-chlorophenyl)-3a,5,6,7,8,8a-hexahydro-8a-pyrrolidino-4H-cyclohept[d]isoxazole-7-carboxylate in 5 ml of concentrated sulfuric acid, 5 ml of acetic acid and ml of water were heated at 120° C. for 5 hours. The separated product was filtered off, washed with water and dried in vacuo to give 3.1 of 3-(4-chlorophenyl)-5,6,7,8-tetrahydro-4H-cyclohept[d]isoxazole-7-carboxylic acid of melting point 215°-217° C.

EXAMPLE 7

1.53 g (0.005 mol) of methyl 3-(4-chlorophenyl)-5,6,7,8-tetrahydro-4H-cyclohept[d]isoxazole-7-carboxylate in 15 ml of tetrahydrofuran were added at -70° C. to a solution of lithium diisopropylamide prepared by adding 3 ml of 2.5M solution of n-butyllithium in hexane over a period of 15 minutes to a solution of 0.77 g (0.0076 mol) of diisopropylamine in 15 ml of tetrahydrofuran cooled to −70° C. After stirring for 30 minutes, 0.78 g (0.0055 mol) of methyl iodide in 5 ml of tetrahydrofuran was added and the mixture wa brought to 20° C. Water and diethyl ether were added. whereupon 1.6 g of methyl 3-(4-chlorophenyl)-5,6.7,8-tetrahydro-7-methyl-4H-cyclohept[d]isoxazole-7-carboxylate were isolated and, after crystallization from methanol melted at 78°-79° C.

EXAMPLE 8

2 g of methyl 3-(4-chlorophenyl)-7-methyl-5,6,7,8-tetrahydro-4H-cyclohept[d]isoxazole-7-carboxylate were treated with 0.5 g of potassium hydroxide in 2 ml of water and 20 ml of methanol at 20° C. for 16 hours. After working-up as described in Example 5 and crystallization from glacial acetic acid, there was obtained 0.9 g of 3-(4-chlorophenyl)-7-methyl-5,6,7,8-tetrahydro-4H-cyclohept[d]isoxazole-7-carboxylic acid of melting point 232°-235° C.

EXAMPLE 9

2 g (0.036 mol) of potassium hydroxide in 8 ml of water were added at 20° C. while stirring to a solution of 6 g (0.016 mol) of a mixture of methyl cis- and trans-4-bromo-3-(4-chlorophenyl)-5,6,7,8-tetrahydro-4H-cyclohept[d]isoxazole-7-carboxylate in 180 ml of methanol. After 20 hours, the solution was filtered and the filtrate was evaporated to a syrup which was dissolved in water and extracted with diethyl ether. The aqueous-alkaline phase was made acid with 2N hydrochloric acid and then extracted with diethyl ether. The ether extract was dried over magnesium sulfate and evaporated. The residue was crystallized from methanol to give 1.2 g of cis-3-(4-chlorophenyl)-5,6,7,8-tetrahydro-4-methoxy-4H-cyclohept-[d]isoxazole-7-carboxylic acid of melting point 168°-170° C.

The trans isomer was isolated from the mother liquor by fractional crystallization. Recrystallization from ethyl acetate gave 1.1 g of trans-3-(4-chlorophenyl)-5,6,7,8-tetrahydro-4-methoxy-4H-cyclohept[d]isoxazole-7-carboxylic acid of melting point 181°-183° C.

The starting material was prepared as follows:

0.989 g (0.0055 mol) of N-bromosuccinimide was added to a solution of 1.52 g (0.005 mol) of methyl 3-(4-chlorophenyl)-5,6,7,8-tetrahydro-4H-cyclohept[- d]isoxazole-7-carboxylate and 0.01 g of dibenzoyl peroxide in 50 ml of carbon tetrachloride. The mixture was heated under reflux for 1.5 hours and then filtered. The filtrate was concentrated to give 1.6 of a cis/trans mixture of methyl 4-bromo-3-(4-chlorophenyl)-5,6,7,8-tetrahydro-4H-cyclohept[d]isoxazole-7-carboxylate; MS m/e 384 (M+H)+.

EXAMPLE 10

A solution of 1.46 g (0.005 mol) of 3-(4-chlorophenyl)-5,6,7,8-tetrahydro-4H-cyclohept[d]isoxazole-7-carboxylic acid in 20 ml of tetrahydrofuran was added slowly at −70° C. to a solution of lithium diisopropylamide prepared by adding 4.4 ml of a 2.5M solution of n-butyllithium in hexane to 1.11 g (0.011 mol) of diisopropylamine in 20 ml of dry tetrahydrofuran at −70° C. After 15 minutes, 0.78 g of methyl iodide was added and the mixture was allowed to warm to 20° C. The mixture was added to water, acidified with 2N hydrochloric acid and extracted with diethyl ether. The resulting mixture of the cis- and trans-3-(4-chlorophenyl)-5,6,7,8-tetrahydro-8-methyl-4H-cyclohept[d]isoxazole-7-carboxylic acid were separated by a combination of crystallization from acetic acid and chromatography on silica gel using toluene/methanol for the elution. There was obtained 0.4 g of cis-3-(4-chlorophenyl)-5,6,7,8-tetrahydro-8-methyl-4H-cyclohept[d]isoxazole-7-carboxylic acid of melting point 230°–233° C. (from acetic acid).

The mother liquor depleted of the cis isomer was chromatographed on silica gel using toluene/methanol (75:25) for the elution and there was obtained, after crystallization from ethyl acetate/hexane, 0.35 g of trans-3-(4-chlorophenyl)-5,6,7,8-tetrahydro-8-methyl-4H-cyclohept[d]isoxazole-7-carboxylic acid of melting point 149°–150° C.

EXAMPLE 11

1 g of 3-(4-chlorophenyl)-4,5,6,7-tetrahydro-1,2-benzisoxazole-5,5-dicarboxylic acid was heated to 200°–210° C. for 5 minutes until effervescence had ceased. The residue was dissolved in ethanol and there was obtained from the solution 0.67 g of 3-(4-chlorophenyl)-4,5,6,7-tetrahydro-1,2-benzisoxazole-5-carboxylic acid of melting point 203°–205° C.

The starting material was prepared as follows:

(A) A solution of 12.1 g (0.05 mol) of diethyl 4-oxocyclohexane-1,1-dicarboxylate, 4.4 g (0.0625 mol) of pyrrolidine and 0.01 g of p-toluenesulfonic acid in 50 ml of benzene was heated under reflux in a Dean-Stark apparatus for 5 hours. Removal of the toluene by evaporation gave 15 g of an oily enamine which was dissolved in 200 ml of diethyl ether.

(B) 3.9 g of triethylamine in 25 ml of diethyl ether were added at −25° C. over a period of 15 minutes while stirring to a solution of 7.8 g of 4-chlorobenzenecarboximidoyl N-hydroxy chloride in 500 ml of dry diethyl ether. After 1 hour the precipitated triethylamine hydrochloride was filtered off and washed with 20 ml of dry diethyl ether which was subsequently combined with the filtrate.

(C) After 1 hour at −10° C., the enamine solution prepared according to paragraph (A) was added to the solution prepared according to paragraph (B) and the mixture was held at 20° C. for 16 hours. After filtration, the filtrate was evaporated to give 18.8 g of diethyl 3-(4-chlorophenyl)-3a-4,5,6,7,7a-hexahydro-7a -pyrrolidino-1,2-benzisoxazole-5,5-dicarboxylate as a golden colored syrup which was used without purification.

(D) A solution of 11 g of diethyl 3-(4-chlorophenyl)-3a-4,5,6,7,7a-hexahydro-7a -pyrrolidino-1,2-benzisoxazole-5,5-dicarboxylate in 500 ml of 2N hydrochloric acid was heated at 125° C. on an oil bath for 3 hours. The oily layer which separated was extracted with diethyl ether to give 7.7 g of diethyl 3-(4-chlorophenyl)-4,5,6,7-tetrahydro-1,2-benzisoxazole-5,5-dicarboxylate which was used without purification.

(E) 7.7 g of diethyl 3-(4-chlorophenyl)-4,5,6,7-tetrahydro-1,2-benzisoxazole-5,5-dicarboxylate were treated with 2.74 g of potassium hydroxide in 16 ml of water and 65 ml of ethanol at 20° C. for 3 days. After removal of the ethanol by evaporation and acidification with 2N hydrochloric acid, the product was taken up in ethyl acetate. There were obtained 6.7 g of 3-(4-chlorophenyl)-4,5,6,7-tetrahydro-1,2-benzisoxazole-5,5-dicarboxylic acid as a buff colored solid of melting point 200°–202° C. (decomposition).

EXAMPLE 12

5.83 g of methyl 3-(4-chlorophenyl)-3a,4,5,6,7,7a-hexahydro-5-methyl-hexahydro-7a-trimethylsilyloxy-1,2-benzisoxazole-5-carboxylate were treated with 20 ml of methanolic hydrogen chloride at 50° C. for 2 minutes to give, after chromatography on silica gel using hexane/diethyl ether (4:1) for the elution, 1.55 g of methyl 3-(4-chlorophenyl)-5,6,7,8-tetrahydro-5-methyl-1,2-benzisoxazole-5-carboxylate as a pale yellow solid of melting point 95°–97° C.

The starting material was prepared as follows:

6.27 g (0.062 mol) of triethylamine in 100 ml of dry diethyl ether were added while stirring at −5° C. over a period of 6 hours to a solution of 11.8 g (0.062 mol) of 4-chlorobenzenecarboximidoyl-N-hydroxy chloride and 7.51 g (0.031 mol) of the trimethylsilyl enol ether of methyl 4-oxo-1-methylcyclohexanecarboxylate in 50 ml of dry diethyl ether. The resulting methyl 3-(4-chlorophenyl)-3a,4,5,6,7,7a-hexahydro-5 -methyl-7a-trimethylsilyloxy-1,2-benzisoxazole-5-carboxylate (9.1 g), obtained after filtration of the ethereal solution, was purified by column chromatography on silica gel using hexane/diethyl ether (4:1) for the elution. There were obtained 5.83 g of methyl 3-(4-chlorophenyl)-3a,4,5,6,7,7a-hexahydro-5-methyl-hexahydro-7a-trimethylsilyloxy-1,2 -benzisoxazole-5-carboxylate as a pale yellow oil; MS: m/e 396 (M+H)+.

EXAMPLE 13

3.26 g of methyl 3-(4-chlorophenyl)-4,5,6,7-tetrahydro-5-methyl-1,2-benzisoxazole-5-carboxylate were heated under reflux with 0.85 g of sodium hydroxide in 5 ml of water and 15 ml of methanol. The methanol was removed by evaporation and there were obtained, after acidification with 2N hydrochloric acid and crystallization from toluene or ethyl acetate, 1.3 g of 3-(4-chlorophenyl)-4,5,6,7-tetrahydro-5-methyl-1,2-benzisoxazole-5-carboxylic acid of melting point 211°–213° C.

EXAMPLE 14

A solution of 0.59 g of ethyl 3-(4-chlorophenyl)-3a,4,5,6,7,7a-hexahydro-7a -pyrrolidino-1,2-benzisoxazole-6-carboxylate (mixture of two diastereoisomers) in 25 ml of 2N hydrochloric acid was heated under reflux for 4 hours. After 1 hour, 0.332 g of a crystalline acid separated out. Crystallization from ethyl acetate/toluene gave 0.23 g of 3-(4-chlorophenyl)-4,5,6,7-tetrahydro-1,2-benzisoxazole-6-carboxylic acid of melting point 227°-228° C.

The starting material was prepared as follows:

(A) A solution of 11.9 g (0.07 mol) of ethyl 3-oxocyclohexanecarboxylate, 7.5 g (0.105 mol) of pyrrolidine and 0.01 g of p-toluenesulfonic acid in 200 ml of toluene was heated under reflux for 7 hours in a Dean-Stark apparatus. The solvent was removed by evaporation and the resulting enamine was taken up in 100 ml of diethyl ether.

(B) 7.8 g (0.077 mol) of triethylamine in 50 ml of dry diethyl ether were added at −20° C. over a period of 0.5 hour while stirring to a solution of 14.6 g (0.077 mol) of 4-chlorobenzenecarboximidoyl-N-hydroxy chloride in 400 ml of dry diethyl ether. After 1 hour the precipitated triethylamine hydrochloride was filtered off and washed with 20 ml of dry diethyl ether which was subsequently combined with the filtrate.

(C) The solution prepared according to paragraph (A) was added to the solution prepared according to paragraph (B) and the mixture was held at 20° C. for 16 hours. The mixture was filtered and there were obtained 17.3 g of a mixture of ethyl 3-(4-chlorophenyl)-3a,4,5,6,7,7a-hexahydro-7a-pyrrolidino-1,2-benzisoxazole-4-carboxylate and ethyl 3-(4-chlorophenyl)-3a,4,5,6,7,7a-hexahydro-7a-pyrrolidino-1,2-benzisoxazole-6-carboxylate which was purified and separated by column chromatography on silica gel using hexane/diethyl ether/ethyl acetate (2:1:1) for the elution. There was firstly eluted ethyl 3-(4-chlorophenyl)- 3a,4,5,6,7,7a-hexahydro-7a-pyrrolidino-1,2-benzisoxazole-4-carboxylate as a mixture of two diastereoisomers. There was subsequently eluted ethyl 3-(4-chlorophenyl)-3a,4,5,6,7,7a-hexahydro-7a-pyrrolidino-1,2-benzisoxazole-6-carboxylate as a mixture of two diastereoisomers.

EXAMPLE 15

A solution of 9.1 g of methyl 3-(4-chlorophenyl)-3a,4,5,6,7,7a -hexahydro-6-methyl-7a-pyrrolidino-1,2-benzisoxazole-6-carboxylate in 100 ml of 2N hydrochloric acid was heated under reflux for 6 hours. The product which separated on cooling was extracted with ethyl acetate and the ethyl acetate extract was dried over magnesium sulfate and evaporated. After crystallization from ethyl acetate/hexane there was obtained 5.3 g of 3-(4-chlorophenyl)-4,5,6,7-tetrahydro-6-methyl-1,2-benzisoxazole-6-carboxylic acid of melting point 185°-187° C.

The foregoing racemic product can be resolved as follows:

A solution of 1.46 g (0.005 mol) of the racemic product and 1.47 g (0.005 mol) of (+)-cinchonine in 35 ml of isopropanol was left to stand at 20° C. for 2 days. The crystalline salt which separated was crystallized from isopropanol and then from ethyl acetate/hexane to give 0.7 g of the cinchonine salt of (−)-3-(4-chlorophenyl)-4,5,6,7-tetrahydro-6-methyl-1,2-benzisoxazole-6-carboxylic acid. The crystals were treated with 2N hydrochloric acid and the mixture was extracted twice with ethyl acetate. The extracts were dried over magnesium sulfate and evaporated and the residue was recrystallized from ethyl acetate/hexane to give 0.28 g of (−)-3-(4-chlorophenyl)-4,5,6,7-tetrahydro-6-methyl-1,2-benzisoxazole-6-carboxylic acid of melting point 169°-170° C.; $[\alpha]^{20}_{589} = -3.8°$ (c=1% in 2N NaOH).

The mother liquors from the resolution were concentrated to half of the original volume and left to stand at 20° C. The crystals which separated were filtered off and recrystallized repeatedly from isopropanol to give the cinchonine salt of (+)-3-(4-chlorophenyl)-4,5,6,7-tetrahydro-6-methyl-1,2-benzisoxazole 6-carboxylic acid in a purity of 95%. After isolation of the acid in a manner analogous to that described in the preceding paragraph followed by crystallization, there was obtained (+)-3-(4-chlorophenyl)-4,5,6,7-tetrahydro-6-methyl-1,2-benzisoxazole-6-carboxylic acid of melting point 165°-168° C.; $[\alpha]^{20}_{589} = +3.5°$ (c=1% in 2N NaOH).

The starting material was prepared as follows:

(A) A solution of 15.6 g of methyl 1-methyl-3-oxocyclohexanecarboxylate, 15.6 g of pyrrolidine and 0.5 g of p-toluenesulfonic acid in 100 ml of xylene was heated under reflux in a Dean-Stark apparatus for 2 hours until water was no longer expelled. The solvent was removed by evaporation and the resulting enamine (21.6 g) was distilled at 97°-102° C./0.3 mmHg to give 17.3 g of an oil which was taken up in 200 ml of diethyl ether.

(B) A solution of 13 g (0.0853 mol) of triethylamine in 100 ml of dry diethyl ether was added at −30° C. over a period of 0.5 hour while stirring to a solution of 22.16 g (0.078 mol) of 4-chlorobenzenecarboximidoyl N-hydroxy chloride in 500 ml of dry diethyl ether. After 1 hour, the precipitated triethylamine hydrochloride was filtered off and washed with 20 ml of dry diethyl ether which was subsequently combined with the filtrate.

(C) The solutions prepared according to paragraphs (A) and (B) were mixed and held at 20° C. for 16.hours. The solution was filtered and the solvent was removed by evaporation to give a mixture of 40 g of methyl 3-(4-chlorophenyl)-3a,4,5,6,7,7a-hexahydro-6-methyl-7a-pyrrolidino-1,2-benzisoxazole-6-carboxylate and methyl 3-(4-chlorophenyl)-3a,4,5,6,7,7a-4-methyl-7a-pyrrolidino-1,2-benzisoxazole-4-carboxylate. Separation was effected by column chromatography on silica gel using hexane/diethyl ether (1:1) for the elution. There were firstly eluted 9.1 g of methyl 3-(4-chlorophenyl-3a,4,5,6,7,7a-hexahydro-6-methyl-7a-pyrrolidino-1,2-benzisoxazole-6-carboxylate.

EXAMPLE 16

A solution of lithium diisopropylamide, prepared from 2.02 g (0.02 mol) of diisopropylamine in 50 ml of dry tetrahydrofuran and 8 ml of a 2.5M solution of n-butyllithium in hexane at −70° C., was treated with 4.07 g (0.0133 mol) of methyl 3-(4-chlorophenyl)-4,5,6,7-tetrahydro-6-methyl-1,2-benzisoxazole-6-carboxylate in 20 ml of tetrahydrofuran at −70° C. 2.08 g (0.0146 mol) of methyl iodide in 20 ml of tetrahydrofuran were added to the resulting red solution at −70° C. over a period of 15 minutes. After 1.5 hours at −70° C., water was added and the product was taken up in ethyl acetate. The ethyl acetate solution was dried over magnesium sulfate and evaporated to give 4.4 g of a mixture of methyl cis- and trans-3-(4-chlorophenyl)-4,5,6,7-tetrahydro-6,7-dimethyl-1,2-benzisoxazole-6-carboxylate as a yellow syrup; MS: m/e 320 (M+H)+.

EXAMPLE 17

A solution of 4.4 g of a mixture of methyl cis- and trans-3-(4-chlorophenyl)-4,5,6,7-tetrahydro-6,7-dimethyl-1,2-benzisoxazole-6-carboxylate in 100 ml of methanol was added to 10 ml of 2N sodium hydroxide solution and the mixture was heated under reflux for 8 hours. After removal of the methanol by evaporation and acidification with 2N hydrochloric acid, the product was crystallized from ethyl acetate/hexane to give 3.1 g of 3-(4-chlorophenyl)-4,5,6,7-tetrahydro-6,7-dimethyl-1,2-benzisoxazole-6-carboxylic acid as a cis-/trans mixture in a ratio of 3:27; melting point 165°–170° C.

EXAMPLE 18

3 g of ethyl exo-3-(4-chlorophenyl)-3a,4,4a,5,5a,5b-hexahydro-5b-pyrrolidinocyclopropa[4,5]cyclopent[1,2-d]isoxazole-5-carboxylate in a mixture of 15 ml of concentrated sulfuric acid, 15 ml of acetic acid and 15 ml of water was heated to reflux for 2 hours. The mixture was cooled and the separated product was filtered off, washed with water and dried in a vacuum. There was obtained 0.93 g of exo-3-(4-chlorophenyl)-4,4a,5,5a-tetrahydrocyclopropa[4,5]cyclopent[1,2-d]isoxazole-5-carboxylic acid which melted at 230°–238° C. (decomposition) after recrystallization from ethyl acetate.

The starting material was prepared as follows:

(A) A solution of 16.8 g (0.1 mol) of ethyl endo/exo-2-oxobicyclo[3:1:0]heptane-6-carboxylate (endo:exo ratio 3:5), 8.7 g (0.11 mol) of pyrrolidine and 0.1 g of p-toluenesulfonic acid in 350 ml of toluene was heated under reflux for 2.5 hours in a Dean-Stark apparatus. The toluene was removed and replaced by 100 ml of diethyl ether.

(B) 11 g (0.11 mol) of triethylamine in 100 ml of dry diethyl ether were added at 20° C. over a period of 1.5 hour while stirring to a solution of 21 g (0.11 mol) of 4-chlorobenzenecarboximidoyl-N-hydroxy chloride in 200 ml of dry diethyl ether. After 1 hour, the precipitated triethylamine hydrochloride was filtered off and washed with 20 ml of dry diethyl ether which was subsequently combined with the filtrate.

(C) The solution prepared according to paragraph (B) was added to the solution prepared according to paragraph (A) and the mixture was held at 5° C. for 24 hours. The solution was then filtered, extracted with 2N hydrochloric acid and the basic products were isolated by basification with 2N aqueous sodium carbonate solution followed by extraction with diethyl ether. There were obtained 20 g of a mixture of ethyl exo-3-(4-chlorophenyl)-3a,4,4a,5,5a,5b-hexahydro-5b-pyrrolidinocyclopropa[4,5]cyclopent[1,2-d]isoxazole-5-carboxylate and ethyl endo-3-(4-chlorophenyl)-3a,4,4a,5,5a,5b-hexahydro-5b-pyrrolidinocyclopropa[4,5]cyclopent[1,2-d]isoxazole-5-carboxylate. The mixture was separated by column chromatography on silica gel using diethyl ether/hexane (1:1) for the elution. There was firstly eluted 0.6 g of ethyl endo-3-(4-chlorophenyl)-3a,4,4a,5,5a,5b-hexahydro-5b-pyrrolidinocyclopropa(4,5-cyclopent[1,2-d]isoxazole-5-carboxylate of melting point 175° C. followed by 5.2 g of ethyl exo-3-(4-chlorophenyl)-3a,4,4a,5,5a,5b-hexahydro-5b-pyrrolidinocyclopropa[4,5]cyclopent[1,2-d]isoxazole-5-carboxylate of melting point 138° C.

EXAMPLE 19

0.7 g of ethyl endo-3-(4-chlorophenyl)-3a,4,4a,5,5a,5b-hexahydro-5b-(N-oxido-1-pyrrolidinyl)-cylopropa[3,4]cyclopent[1,2-d]isoxazole-5-carboxylate was heated at 120° C. in an oil bath. There was obtained 0.45 g of ethyl endo-3-(4-chlorophenyl)-4,4a,5,5a-tetrahydrocyclopropa[4,5]cyclopent[1,2-d]-isoxazole-5-carboxylate.

The starting material was prepared as follows:

0.303 g (0.0015 mol) of m-chloroperbenzoic acid in 20 ml of chloroform was added over a period of 5 minutes to a solution of 0.56 g (0.0015 mol) of ethyl endo-3-(4-chlorophenyl)-3a,4,4a,5,5a,5b-hexahydro-5b-pyrrolidinocyclopropa[4,5]cyclopent[1,2-d]isoxazole-5-carboxylate (prepared as described in Example 18) in 25 ml of chloroform. After 16 hours, the chloroform was removed by evaporation to give 0.7 g of ethyl endo-3-(4-chlorophenyl)-3a,4,4a,5,5a,5b-hexahydro-5b-(N-oxido-1-pyrrolidinyl)-cyclopropa[3,4]cyclopent[1,2-d]isoxazole-5-carboxylate of melting point 110°–115° C.

EXAMPLE 20

0.6 g of ethyl endo-3-(4-chlorophenyl)-4,4a,5,5a-tetrahydrocyclopropa[4,5]cyclopent[1,2-d]isoxazole-5-carboxylate was treated with 0.42 g of potassium hydroxide in 1.5 ml of water and 75 ml of methanol at 50° C. for 40 hours. Acidification with 2N hydrochloric acid gave 0.3 g of endo-3-(4-chlorophenyl)-4,4a,5,5a-tetrahydrocyclopropa[4,5]cyclopent[1,2-d]isoxazole-5-carboxylic acid of melting point 188°–192° C. (from ethyl acetate/hexane).

EXAMPLE 21

2 g of ethyl exo-3(4-chlorophenyl)-3a,5,5a,6,6a,6b-hexahydro-6b-pyrrolidino-4H-cyclopropa[g]-1,2-benzisoxazole-6-carboxylate (diastereoisomer II) were heated to reflux with 80 ml of 20% methanolic hydrogen chloride for 16 hours. The methanol was removed by evaporation and the residue was treated with water. The product was taken up in diethyl ether and the solution was dried over sodium sulfate and evaporated. There was obtained 0.8 g of methyl exo-3-(4-chlorophenyl-5,5a,6,6a-tetrahydro-4H-cyclopropa[g]-1,2-benzisoxazole-6-carboxylate of melting point 130°–132° C.

The starting material was prepared as follows:

(A) A solution of 31.40 g (0.17 mol) of ethyl endo/exo-2-oxobicyclo[4:1:0]heptanecarboxylate (endo:exo ratio 10:80), 15.6 g (0.19 mol) of pyrrolidine and 0.01 g of p-toluenesulfonic acid in 500 ml of dry toluene was heated under reflux for 2 hours until water was no longer produced. The toluene was removed and replaced by 100 ml of dry diethyl ether.

(B) A solution of 18.9 g (0.19 mol) of triethylamine in 100 ml of dry diethyl ether was added at 5° C. over a period of 15 minutes while stirring to a solution of 35.53 g (0.19 mol) of 4-chlorobenzenecarboximidoyl-N-hydroxy chloride in 400 ml of dry diethyl ether. After 1 hour, the precipitated triethylamine hydrochloride wa filtered off and washed with 20 ml of dry diethyl ether which was subsequently combined with the filtrate.

(C) The solution prepared according to paragraph (B) was added to the solution prepared according to paragraph (A). After 16 hours, the mixture was filtered and extracted three times with 2N hydrochloric acid each time. Basification with 2N sodium carbonate solution and extraction with diethyl ether gave a mixture of two diastereoisomers having the exo configuration and one diastereoisomer having the endo configuration. The mixture separated by column chromatography on silica gel using hexane/diethyl ether (2:1) for the elution, with the adducts being eluted in the following order: ethyl endo-3-(4-chlorophenyl)-3a,5,5a,6,6a,6b-hexahydro-6b-pyrrolidino-4H-cyclopropa[g]-1,2-benzisoxazole-6-carboxylate of melting point 150°–153° C.; ethyl exo-3-(4-chlorophenyl)-3a,5,5a,6,6a,6b-hexahydro-6b-pyrrolidino-4H-cyclopropa[g]-1,2-benzisoxazole-6-carboxylate (diastereoisomer I) of melting point 137°–140°

C. and ethyl exo-3-(4-chlorophenyl)-3a,5,5a,6,6a,6b-hexahydro-6b-pyrrolidino-4H-cyclopropa[g]-1,2-benzisoxazole-6-carboxylate (diastereoisomer II) of melting point 153°-155° C.

EXAMPLE 22

1.1 g of methyl exo-3-(4-chlorophenyl)-5,5a,6,6a-tetrahydro-4H-cyclopropa[g]-1,2-benzisoxazole-6-carboxylate were treated with 0.2 g of potassium hydroxide in 2 ml of water and 40 ml of methanol for 5.5 hours at 60° C. After working-up as described in Example 5, there was obtained 0.6 g of exo-3-(4-chlorophenyl)-5,5a,6,6a-tetrahydro-4H -cyclopropa[g]-1,2-benzisoxazole-6-carboxylic acid of melting point 280°-283° C. (from acetic acid).

EXAMPLE 23

1.8 g of ethyl endo-3-(4-chlorophenyl)-3a,5,5a,6,6a, 6b-hexahydro-6b-pyrrolidino-4H-cyclopropa[g]-1,2-benzisoxazole-6-carboxylate (prepared as described in Example 21) in 5 ml of concentrated sulfuric acid, 5 ml of glacial acetic acid and 5 ml of water was heated at 110° C. for 2 hours. The crystals obtained upon cooling the solution were filtered off, washed with water and dried in a vacuum. There was obtained 0.4 g of crude product which was crystallized from acetic acid to give 0.3 g of endo-3-(4-chlorophenyl)-5,5a,6,6a-tetrahydro-4H-cyclopropa[g]-1,2-benzisoxazole-6-carboxylic acid of melting point 198°-200° C.

EXAMPLE 24

0.5 g of ethyl endo-3-(4-chlorophenyl)-3a,4a,5,5a, 6,6a-hexahydro-3a-bromo-4H -cyclopropa[f]-1,2-benzisoxazole-5-carboxylate in 30 ml of methanol was treated with 1.4 g of potassium hydroxide in 6 ml of water at 20° C. for 24 hours. After removal of the methanol by evaporation and acidification with 2N hydrochloric acid followed by crystallization from methanol, there was obtained 0.21 g of endo-3-(4-chlorophenyl)-4a,5,5a,6 -tetrahydro-4H-cyclopropa[f]-1,2-benzisoxazole-5-carboxylic acid of melting point 204°-205° C.

The starting material was prepared as follows:

7.57 g (0.075 mol) of triethylamine in 150 ml of diethyl ether were added at 5° C. while stirring over a period of 0.5 hour to a solution of 14.28 g (0.075 mol) of 4-chlorobenzenecarboximidoyl-N-hydroxy chloride in 150 ml of diethyl ether. After an additional 15 minutes, the mixture was filtered. The filtrate was treated with 46.78 g (0.277 mol) of ethyl-endo/exo-bicyclo[4:1:0] hept-3-ene-7-carboxylate (endo:exo ratio 1:3) and the solvent was removed by evaporation. After standing at 20° C. for 24 hours, the mixture was filtered and the excess ester starting material was removed by distillation at 75°-86° C./0.1 mmHg. There was obtained a mixture of two diastereoisomers of ethyl endo-3-(4-chlorophenyl)-3a,4a,5,5a,6,6a-hexahydro-4H-cyclopropa[f]-1,2-benzisoxazole-5-carboxylate (isomers A and B) and two diastereoisomers of ethyl exo-3-(4-chlorophenyl)-3a,4a,5,5a,6,6a-hexahydro-4H-cyclopropa[f]-1,2-benzisoxazole-5-carboxylate (isomers C and D). This mixture was separated by column chromatography on silica gel using diethyl ether/hexane (1:1) for the elution. Isomers A and B were collected together as the first fractions and isomers C and D were collected together as later fractions. The major isomer (C) of ethyl exo-3-(4-chlorophenyl)-3a,4a,5,5a,6,6a-hexahydro-4H-cyclopropa[f]-1,2-benzisoxazole-5-carboxylate was isolated by crystallization from diethyl ether and melted at 122° C. The major endo isomer (A) of ethyl endo-3-(4-chlorophenyl)-3a,4a,5,5a,6,6a-hexahydro-4H-cyclopropa[f]-1,2-benzisoxazole-5-carboxylate crystallized from diethyl ether/hexane and melted at 128°-130° C.

0.89 g (0.005 mol) of N-bromosuccinimide and 0.01 g of dibenzoyl peroxide were added to a solution of 1.59 g (0.005 mol) of ethyl endo-3-(4-chlorophenyl)-3a,-4a,5,6,6a-hexahydro-4H-cyclopropa[f]-1,2-benzisoxazole-5-carboxylate (isomer A) in 30 ml of carbon tetrachloride. After heating under reflux for 1.5 hours, the solution was cooled and the separated succinimide was removed by filtration. The crude product was purified by chromatography on silica gel using diethyl ether/hexane (1:1) for the elution and was crystallized from ethanol to give 0.51 g of ethyl endo-(3-(4-chlorophenyl)-3a,4a,5,6,6a-hexahydro-3a-bromo-4H-cyclopropa[f]-1,2-benzoxazole-5-carboxylate of melting point 118°-119° C.

EXAMPLE 25

1 g of ethyl exo-3-(4-chlorophenyl)-3a,4a,5,5a,6,6a-hexahydro-3a-bromo-4H -cyclopropa[f]-1,2-benzisoxazole-5-carboxylate was dissolved in 20 ml of methanol and treated with 1 g of potassium hydroxide in 2 ml of water at 20° C. for 16 hours. After working-up as described in Example 5, there was obtained 0.6 g of exo-3-(4-chlorophenyl)-4a,5,5a,6-tetrahydro-4H-cyclopropa[f]-1,2-benzisoxazole-5-carboxylic acid of melting point 245°-246° C. (from methanol).

The starting material was prepared by brominating 1.59 g of ethyl exo-3-(4-chlorophenyl)-3a,4a,5,5a,6,6a-hexahydro-4H-cyclopropa[f]-1,2-benzisoxazole-5-carboxylate (see Example 24) in 30 ml of carbon tetrachloride with 0.89 g of N-bromosuccinimide in a manner analogous to that described in Example 24. There was obtained 1.6 g of ethyl exo-3-(4-chlorophenyl)-3a,4a,5-,5a,6,6a -hexahydro-3a-bromo-4H-cyclopropa[f]-1,2-benxisoxazole-5-carboxylate.

EXAMPLE 26

A solution of 3.12 g (0.02 mol) of 3-oxocyclohexanecarboxylate, 1.91 g (0.022 mol) of morpholine and 0.01 g of p-toluenesulfonic acid in 300 ml of toluene was heated under reflux for 6 hours in a Dean-Stark apparatus. The solution was cooled to 0° C. and there were added 2.02 g (0.02 mol) of triethylamine in 5 ml of toluene followed by 3.83 g (0.02 mol) of p-chlorobenzoyl chloride in 30 ml of toluene over a period of 0.5 hour. The mixture was stirred at 20° C. for 3 hours and then heated at 60° C. for 3 hours. The solution was cooled and filtered. The filtrate was evaporated to give ethyl 2-(4-chlorobenzoyl)-1-morpholino-4-cyclohexenecarboxylate as a gum which was dissolved in 10 ml of ethanol and 5 ml of pyridine and treated with 1.4 g (0.02 mol) of hydroxylamine hydrochloride. The mixture was then heated under reflux for 2 hours. The solvents were removed by evaporation, 2N hydrochloric acid was added to the residue and the product was extracted with diethyl ether. Evaporation of the ethereal extract gave 1 g of methyl 3-(4-chlorophenyl)-4,5,6,7-tetrahydro-2,1-benzisoxazole-6-carboxylate of melting point 141°-143° C. (from ethyl acetate/hexane).

EXAMPLE 27

1 g of methyl 3-(4-chlorophenyl)-4,5,6,7-tetrahydro-2,1-benzisoxazole-6-carboxylate was treated with 0.5 g of potassium hydroxide in 2 ml of water and 15 ml of methanol at 20° C. After working-up as described in Example 5 there was obtained, after crystallization from acetic acid, 0.45 g of 3-(4-chlorophenyl)-4,5,6,7-tetrahydro-2,1-benzisoxazole-6-carboxylic acid of melting point 221°–224° C.

EXAMPLE 28

In a manner analogous to that described in Example 26, from 7.28 g (0.04 mol) of ethyl exo-bicyclo[4:1:0-]heptane-7-carboxylate, 3.84 g (0.044 mol) of morpholine and 0.01 g of p-toluenesulfonic acid in 150 ml of toluene there was obtained the corresponding enamine. This was treated with 4.1 g (0.04 mol) of triethylamine followed by the dropwise addition of 7.5 g of p-chlorobenzoyl chloride and subsequent heating at 60° C. for 6 hours. The resulting ethyl exo-3-(4-chlorobenzoyl)-2-morpholinobicyclo[4.1.0]hept-2-ene-7-carboxylate was reacted in 20 ml of ethanol and 10 ml of pyridine with 2.8 g of hydroxylamine hydrochloride. After heating under reflux for 3 hours, there were obtained 18 g of a syrup which was purified by column chromatography on silica gel using hexane/ethyl acetate (4:1) for the elution. There were obtained 2.8 g of ethyl exo-3-(4-chlorophenyl)-5,5a,6,6a-tetrahydro-4H-cyclopropa[g]-2,1-benzisoxazole-6-carboxylate of melting point 109°–110° C.

EXAMPLE 29

2.8 g of ethyl exo-3-(4-chlorophenyl)-5,5a,6,6a-tetrahydro-4H-cyclopropa[g]-2,1-benzisoxazole-6-carboxylate were treated with 1 g of potassium hydroxide in 3 ml of water and 100 ml of methanol at 40° C. for 8 hours. After working-up as described in Example 5, there was obtained 2.1 g of exo-3-(4-chlorophenyl)-5,5a,6,6a-tetrahydro-4H-cyclopropa[g]-2,1-benzisoxazole-6-carboxylic acid of melting point 282°–285° C. (from glacial acetic acid).

EXAMPLE 30

In a manner analogous to that described in Example 26, from 8.56 g (0.047 mol) of ethyl endo-bicyclo[4:1:0-]heptane-7-carboxylate, 4.52 g (0.05 mol) of morpholine and 0.01 g of p-toluenesulfonic acid, there was obtained the corresponding enamine which was reacted with 8.23 g (0.047 mol) of p-chlorobenzoyl chloride in the presence of 4.75 g (0.047 mol) of triethylamine. The resulting ethyl endo-3-(4-chlorobenzoyl)-2-morpholinobicyclo[4.1.0]hept-2-ene-7-carboxylate, without purification, was treated with 3.27 g (0.047 mol) of hydroxylamine hydrochloride in 25 ml of ethanol and 12.5 g of pyridine and the mixture was heated under reflux for 3 hours. Purification by column chromatography on silica gel using hexane/ethyl acetate (4:1) for the elution gave 0.6 g of pure ethyl endo-3-(4-chlorophenyl)-5,5a,6,6a-tetrahydro-4H-cyclopropa[g]-2,1-benzisoxazole-6-carboxylate of melting point 110° C. (from hexane/ethyl acetate.

EXAMPLE 31

0.37 g of ethyl endo-3-(4-chlorophenyl)-5,5a,6,6a-tetrahydro-4H-cyclopropa[g]-2,1-benzisoxazole-6-carboxylate in 12 ml of concentrated sulfuric acid were left to stand at 20° C. for 2–3 days. The mixture was added to water and the product was isolated by partitioning between diethyl ether and dilute sodium carbonate solution. The aqueous-alkaline phase was acidified with 2N hydrochloric acid and the precipitate formed was filtered off and dried in a vacuum. There was obtained 0.15 g of endo-3-(4-chlorophenyl)-5,5a,6,6a-tetrahydro-4H-cyclopropa[g]-2,1-benzisoxazole-6-carboxylic acid of melting point 196°–199° C. after crystallization from ethyl acetate/hexane.

EXAMPLE 32

2 g of dry diatomaceous earth were stirred in 15 ml of dry benzene and 2 g (9 mmol) of phosphorus pentasulfide and 0.4 g (1.6 mmol) of 2,3,5,6-tetrachloro-p-benzoquinone was added. 0.5 g (1.62 mmol) of methyl 4-[(4-chlorophenyl)(amino)methylene]-3-oxocycloheptanecarboxylate was added and the mixture was heated under reflux for 0.5 hour. The mixture was filtered and the filter cake was washed with six 20 ml portions of hot ethyl acetate. The combined filtrate and washings were evaporated and the residue, after chromatography on silica gel using 30% ethyl acetate/hexane for the elution and recrystallization from methylcyclohexane, gave 0.18 g of methyl 3-(4-chlorophenyl)-5,6,7,8-tetrahydro-4H-cyclohept[d]isothiazole-7-carboxylate of melting point 108°–109° C.

The starting material was prepared as follows:

0.22 g of methyl 3-(4-chlorophenyl)-5,6,7,8-tetrahydro-4H-cyclohept[d]isoxazole-7-carboxylate was dissolved in 12 ml of methanol, 0.19 g of wet Raney-nickel was added and the mixture was hydrogenolyzed at 3.4 atmospheres and at room temperature for 30 hours. The catalyst was removed by filtration and washed on the filter firstly with ethanol and then with dichloromethane. The filtrate was evaporated and the residue was purified by chromatography on silica gel using ethyl acetate for the elution. There was obtained 0.155 g of methyl 4-[(4-chlorophenyl)(amino)methylene]-3-oxocycloheptanecarboxylate of melting point 154°–155° C.

EXAMPLE 33

0.18 g (0.56 mmol) of methyl 3-(4-chlorophenyl)-5,6,7,8-tetrahydro-4H-cyclohepta[d]isothiazole-7-carboxylate was dissolved in 10 ml of methanol and 0.5 ml of 25% aqueous sodium hydroxide solution was added. The mixture was heated under reflux for 0.25 hour. The mixture was then evaporated and the residue was dissolved in 30 ml of water and acidified with dilute hydrochloric acid. The mixture was extracted three times with 25 ml of dichloromethane each time and the combined extracts were dried over magnesium sulfate and evaporated to give, after recrystallization from acetonitrile, 0.115 g of 3-(4-chlorophenyl)-5,6,7,8-tetrahydro-4H -cyclohept[d]isothiazole-7-carboxylic acid of melting point 184°–185° C.

EXAMPLE 34

(A) 0.04 g (1 mmol) of a 60% dispersion of sodium hydride in mineral oil was added under a nitrogen atmosphere while stirring to 6 ml of dry 1,2-dimethoxyethane. A solution of 0.11 g (1.2 mmol) of phenol in 4 ml of dry 1,2-dimethoxyethane was added dropwise over a period of 0.25 hour and the solution was stirred at room temperature for 0.5 hour.

(B) 0.385 g (1 mmol) of a cis/trans mixture of methyl 4bromo-3-(4-chlorophenyl)-5,6,7,8-tetrahydro-4H-cyclohept[d]isoxazole-7-carboxylate, prepared as described in Example 9, in 4 ml of dry 1,2-dimethoxyethane was stirred at room temperature and the sodium phenoxide solution prepared according to paragraph (A) was added dropwise. The mixture was stirred for 4 hours. Water was added and the mixture was partially evaporated and extracted three times with dichloromethane. The combined dichloromethane extracts were dried over magnesium sulfate and evaporated, and the residue was purified by chromatography on silica gel using dichloromethane for the elution. There was obtained 0.16 g of a cis/trans mixture of methyl 3-(4-chlorophenyl)-5,6,7,8-tetrahydro-4-phenoxy-4H-cyclohepta[d]isoxazole-7-carboxylate of melting point 85°–87° C.

EXAMPLE 35

0.08 g (0.2 mmol) of a cis/trans mixture of methyl 3-(4-chlorophenyl)-5,6,7,8-tetrahydro-4-phenoxy-4H-cyclohept[d]isoxazole-7-carboxylate was stirred with 5 ml of methanol and 0.5 ml of 25% aqueous sodium hydroxide solution at room temperature for 3 hours. Water was added and the mixture was washed twice with diethyl ether. The aqueous phase was acidified with dilute hydrochloric acid and extracted three times with dichloromethane. The combined organic extracts were dried over magnesium sulfate and evaporated to give, after recrystallization from toluene/methylcyclohexane, 0.038 g of a cis/trans mixture of 3-(4-chlorophenyl)-5,6,7,8-tetrahydro-4-phenoxy-4H-cyclohept[d]isoxazole-7-carboxylic acid of melting point 145°–146° C.

Two recrystallizations of the above cis/trans mixture from acetonitrile gave trans-3-(4-chlorophenyl)-5,6,7,8-tetrahydro-4-phenoxy-4H-cyclohepta[d]isoxazole-7-carboxylic acid of melting point 182°–183° C. The cis isomer can be obtained from the mother liquors using high pressure liquid chromatography.

EXAMPLE 36

0.13 g (0.34 mmol) of a cis/trans mixture of methyl 4-bromo-3-(4-chlorophenyl)-5,6,7,8-tetrahydro-4H-cyclohept[d]isoxazole-7-carboxylate, prepared as described in Example 9, in 2 ml of 1,2-dimethoxyethane was stirred at room temperature with 0.046 g (0.7 mmol) of sodium azide for 24 hours. 30 ml of water were added and the mixture was extracted three times with dichloromethane. The combined extracts were dried over magnesium sulfate and evaporated to give, after recrystallization from hexane, 0.078 g of methyl trans-4-azido-3-(4-chlorophenyl)-5,6,7,8-tetrahydro-4H-cyclohepta[d]isoxazole-7-carboxylate of melting point 78°–79° C.

EXAMPLE 37

0.15 g (0.43 mmol) of methyl trans-4-azido-3-(4-chlorophenyl)-5,6,7,8-tetrahydro-4H-cyclohept[d]isoxazole-7-carboxylate was stirred in 7.5 ml of methanol and 0.6 ml of 25% aqueous sodium hydroxide solution was added. The mixture was then stirred at room temperature for 2 hours. Water was added. The methanol was removed by evaporation and the aqueous phase was washed with diethyl ether, acidified with dilute hydrochloric acid and. extracted twice with dichloromethane. The combined dichloromethane extracts were dried over magnesium sulfate and evaporated to give, after recrystallization from ethyl acetate/hexane and subsequently from ethanol, 0.025 g of a cis/trans mixture of 4-azido-3-(4-chlorophenyl)-5,6,7,8-tetrahydro-4H-cyclohept[d]isoxazole-7-carboxylic acid of melting point 157°–159° C.

EXAMPLE 38

A solution of 4.7 g (12 mmol) of methyl 3-(4-chlorophenyl)-6-ethyl-3a,4,5,6,7,7a-hexahydro-7a-pyrrolidino-1,2-benzisoxazole-6-carboxylate in 200 ml of 2N hydrochloric acid was heated under reflux for 6 hours. The mixture was extracted with diethyl ether and the extracts were dried over magnesium sulfate and evaporated. After crystallization from methylcyclohexane, there were obtained 1.58 g of methyl 3-(4-chlorophenyl)-6-ethyl-4,5,6,7-tetrahydro-1,2-benzisoxazole-6-carboxylate of melting point 101°–102.5° C.

The starting material was prepared as follows:

(A) A solution of 9.83 g (0.053 mol) of methyl 1-ethyl-3-oxocyclohexane carboxylate, 7.6 g (0.106 mol) of pyrrolidine and 0.01 g of p-toluenesulfonic acid in 100 ml of dry toluene was heated under reflux in a DeanStark apparatus for 16 hours. The solvent was removed by evaporation to give 13 g of enamine which was taken up in 200 ml of dry diethyl ether.

(B) 8.9 g (0.088 mol) of triethylamine in 75 ml of dry diethyl ether were added over a period of 0.5 hour at −20° C. while stirring to a solution of 15.2 g (0.08.mol) of 4-chlorobenzenecarboximidoyl N-hydroxy chloride in 350 ml of dry diethyl ether. After 1 hour, the precipitated triethylamine hydrochloride was filtered off and washed with 20 ml of dry diethyl ether which was subsequently combined with the filtrate.

(C) The solution prepared according to paragraph (A) was added to the mixture prepared according to paragraph (B) over a period of 0.5 hour and the mixture was stirred at 20° C. for 16 hours. The mixture was filtered and there were obtained 24.3 g of a mixture of methyl 3-(4-chlorophenyl)-6-ethyl-3a,4,5,6,7,7a-hexahydro-7a-pyrrolidino-1,2-benzisoxazole-6-carboxylate and methyl 3-(4-chlorophenyl)-4-ethyl-3a,4,5,6,7,7a-hexahydro-7a-pyrrolidino-1,2-benzisoxazole-4-carboxylate which was purified and separated by column chromatography on silica gel using hexane/ethyl acetate (1:1) for the elution. There was firstly eluted methyl 3-(4-chlorophenyl)-6-ethyl-3a,4,5,6,7,7a-hexahydro-7a-pyrrolidino-1,2-benzisoxazole-6-carboxylate and subsequently methyl 3-(4-chlorophenyl)-4-ethyl-3a,4,5,6,7,,7a-hexahydro-7a-pyrrolidino-1,2-benzisoxazole-4-carboxylate.

EXAMPLE 39

1.5 g (4.7 mmol) of methyl 3-(4-chlorophenyl)-6-ethyl-4,5,6,7-tetrahydro-1,2-benzisoxazole-6-carboxylate were heated under reflux with 5.25 ml of 2N sodium hydroxide solution, 5.25 ml of water and 50 ml of methanol for 30 hours. The methanol was then removed by evaporation. By acidification with 2N hydrochloric acid followed by extraction with ethyl acetate there were obtained, after crystallization from hexane/ethyl acetate, 1.02 g of 3-(4-chlorophenyl)-6-ethyl-4,5,6,7-tetrahydro-1,2-benzisoxazole-6-carboxylic acid of melting point 223°–226° C.

EXAMPLE 40

0.09 g of sodium hydroxide in 2 ml of water was added at 20° C. while stirring to a solution of 0.44 g of a mixture of methyl cis- and trans-4-bromo-3-(4-chlorophenyl)-4,5,6,7-tetrahydro-1,2-benzisoxazole-6-carboxylate in 15 ml of methanol. After 3 hours, the methanol was removed by evaporation. Water was added and the mixture was extracted with diethyl ether. The aqueous phase was acidified with 2N sulfuric acid, whereupon a precipitate formed. This precipitate was collected and crystallized from ethanol to give 100 mg of 3-(4-chlorophenyl)-4,5,6,7-tetrahydro-4-methoxy-1,2- benzisoxazole-6-carboxylic acid (cis:trans ratio 2:1) of melting point 190°–191° C.

The starting material was prepared as follows:

(a) 1.95 g (0.011 mol) of N-bromosuccinimide were added to a solution of 2.91 g (0.01 mol) of methyl 3-(4-chlorophenyl)-4,5,6,7-tetrahydro-1,2-benzisoxazole-6-carboxylate and 0.01 g of dibenzoyl peroxide in 100 ml of carbon tetrachloride. The mixture was heated under reflux for 3 hours and then filtered. The filtrate was concentrated and the residue was crystallized from ethyl acetate/hexane to give 1.54 g of a mixture of methyl cis- and trans-4-bromo-3-(4-chlorophenyl)-4,5,6,7-tetrahydro-1,2-benzisoxazole-6-carboxylate of melting point 121°–124° C.

EXAMPLE 41

1.1 g (0.003 mol) of a mixture of methyl cis- and trans-4-bromo-3-(4-chlorophenyl)-4,5,6,7-tetrahydro-1,2-benzisoxazole-6-carboxylate were dissolved in 10 ml of warm methanol and added to a solution of 0.1 g of sodium in 20 ml of methanol. The mixture was held at 40° C. for 2 hours and the methanol was then removed by evaporation. The resulting syrup was purified by column chromatography on silica gel using hexane/ethyl acetate (4:1) for the elution. There was obtained as the major product 0.32 g of methyl trans-3-(4-chlorophenyl)-4,5,6,7-tetrahydro-4-methoxy-1,2-benzisoxazole-6-carboxylate; NMR: $\delta$ CDCl$_3$: 7.72 (m, 2H), 7.42 (m, 2H), 4.31 (m, 1H), 3.74 (s, 3H), 3.42 (s, 3H), 3.24–3.07 (m, 2H), 2.95–2.57 (m, 2H), 1.65 (m, 1H).

EXAMPLE 42

0.32 g (0.001 mol) of methyl trans-3-(4-chlorophenyl)-4,5,6,7-tetrahydro-4-methoxy-1,2-benzisoxazole-6-carboxylate was stirred in a solution of 10 ml of methanol, 10 ml of water and 0.4 g of sodium hydroxide at 20° C. for 16 hours. The methanol was removed by evaporation and an excess of water was added. The solution was acidified with 2N hydrochloric acid and the resulting precipitate was extracted into ethyl acetate. The solution was washed with sodium chloride solution, dried over magnesium sulfate and evaporated. Crystallization of the resulting solid from ethyl acetate/hexane gave 0.1 g of trans-3-(4-chlorophenyl)-4,5,6,7-tetrahydro-4-methoxy-1,2-benzisoxazole-6α-carboxylic acid of melting point 193°–195° C.

EXAMPLE 43

A solution of 3.46 g (0.0125 mol) of racemic 3-(4-chlorophenyl)-4,5,6,7-tetrahydro-1,2-benzisoxazole-6-carboxylic acid in 50 ml of dry tetrahydrofuran was added slowly at −70° C. to a solution of lithium diisopropylamide prepared by adding 10 ml of a 2.5M solution of n-butyllithium in hexane to 2.53 g (0.025 mol) of diisopropyl amine in 25 ml of dry tetrahydrofuran at −70° C. After 15 minutes, 2 g (0.014 mol) of methyl iodide were added and the mixture was allowed to warm to 20° C. over a period of 1.5 hours. The mixture was added to water, acidified with 2N hydrochloric acid and extracted with diethyl ether. The resulting mixture of cis- and trans-3-(4-chlorophenyl)-4,5,6,7-tetrahydro-7-methyl-1,2-benzisoxazole-6-carboxylic acids was separated by repeated crystallization from acetic acid. The cis-3-(4-chlorophenyl)-4,5,6,7-tetrahydro-7-methyl-1,2-benzisoxazole-6-carboxylic acid separated first, there being obtained 0.78 g of melting point 238°–241° C. The mother liquor yielded 0.79 g of trans-3-(4-chlorophenyl)-4,5,6,7-tetrahydro-7-methyl-1,2-benzisoxazole-6-carboxylic acid of melting point 183°–186° C.

EXAMPLE 44

3.5 g of methyl 3-(4-chlorophenyl)-3a,4,5,6,7,8,9,9a-octahydro-9a-pyrrolidino-cyclooct[d]isoxazole-8-carboxylic acid were heated under reflux for 5 hours in a mixture of 10% methanolic hydrochloric acid. The mixture was concentrated to a volume of half and there were obtained 2.55 g of methyl 3-(4-chlorophenyl)-4,5,6,7,8,9-hexahydrocyclooct[d]isoxazole-8-carboxylate of melting point 65°–69° C.

The starting material was prepared as follows:

(A) A solution of 3.68 g (0.02 mol) of methyl 3-oxocyclooctane carboxylate, 1.56 g (0.022 mol) of pyrrolidine and 0.005 g of p-toluenesulfonic acid in 30 ml of dry toluene was heated under reflux for 3 hours in a Dean-Stark apparatus. The solvent was removed by evaporation to give the enamine which was dissolved in 60 ml of dry diethyl ether.

(B) 2.22 g (0.022 mol) of triethylamine in 50 ml of dry diethyl ether were added at 5° C. to a solution of 4.18 g (0.022 mol) of 4-chlorobenzenecarboximidoyl N-hydroxy chloride in 100 ml of dry diethyl ether over a period of 0.5 hour while stirring. After 1 hour, the precipitated triethylamine hydrochloride was filtered off and washed with 20 ml of dry diethyl ether which was subsequently combined with the filtrate.

(C) The solutions obtained according to paragraphs (A) and (B) were cooled to 0° C., mixed together and held at 0°–5° C. for 2 hours and then at 20° C. for 16 hours. 2.1 g of methyl 3-(4-chlorophenyl)-3a,4,5,6,7,8,9,9a-octahydro-9a-pyrrolidino-cyclooct[d]isoxazole-8-carboxylate of melting point 146°–147° C. precipitated in crystalline form from the reaction mixture and were filtered off. Concentration of the filtrate to half of the original volume gave an additional 1.5 g of the same product of melting point 144°–145° C.

EXAMPLE 45

2.4 g (0.039 mol) of methyl 3-(4-chlorophenyl)-4,5,6,7,8,9-hexahydrocyclooct[d]isoxazole-8-carboxylate were stirred for 18 hours in 10 ml of methanol, 0.5 g of potassium hydroxide and 2 ml of water. The methanol was removed by evaporation and the residual gum was dissolved in water. Acidification with a few drops of concentrated hydrochloric acid gave a white granular precipitate which was filtered off, washed with water and dried. After crystallization from glacial acetic acid, there were obtained 1.9 g of 3-(4-chlorophenyl)-4,5,6,7,8,9-hexahydrocyclooct[d]isoxazole-8-carboxylic acid of melting point 215° C.

EXAMPLE 46

A solution of 0.865 g (0.0031 mol) of 3-(4-chlorophenyl)-4,5,6,7-tetrahydro-1,2-benzisoxazole-6-carboxylic acid in 20 ml of dry tetrahydrofuran was added slowly at −70° C. to a solution of lithium diisopropylamide prepared by adding 2.65 ml of a 2.5M solution of n-butyllithium in hexane to 0.66 g (0.0065 mol) of diisopropylamine in 20 ml of dry tetrahydrofuran at −70° C. After 0.25 hour a deep red solution had formed. 0.53 g (0.0031 mol) of isopropyl iodide in 5 ml of dry tetrahydrofuran was added and the mixture was stirred at −65° C. to −30° C. for 1 hour and at a temperature up to 5° C. for an additional 1 hour. The resulting yellow solution was poured into an excess of water and acidified with 2N hydrochloric acid. The mixture was extracted four times with diethyl ether and the combined ether extracts were washed with sodium chloride solution and dried over magnesium sulfate. Evaporation gave a yellow solid which, after crystallization from glacial acetic acid, yielded 0.53 g of trans-3-(4-chlorophenyl)-4,5,6,7-tetrahydro-7-isopropyl-1,2-benzisoxazole-6--carboxylic acid of melting point 180°–182° C.

EXAMPLE 47

A solution of 1.73 g (0.00625 mol) of 3-(4-chlorophenyl)-4,5,6,7-tetrahydro-1,2-benzisoxazole-6-carboxylic acid in 30 ml of dry tetrahydrofuran was added slowly at −70° C. to a solution of lithium diisopropylamide prepared by adding 5.25 ml of a 2.5M solution of n-butyllithium in hexane to 1.32 g (0.013 mol) of diisopropylamine in 20 ml of dry tetrahydrofuran at −70° C. After 0.25 hour a deep red color had developed. 1.05 g (0.0067 mol) of ethyl iodide in 5 ml of dry tetrahydrofuran were added and the temperature was allowed to rise to −20° C. over a period of 1.25 hours. The resulting light brown solution was poured into an excess of water and acidified with 2N hydrochloric acid. The mixture was extracted four times with diethyl ether and the combined ether extracts were washed with sodium chloride solution, dried over magnesium sulfate and evaporated. The residue was crystallized twice from glacial acetic acid and there was obtained 0.36 g of trans-3-(4-chlorophenyl)-7-ethyl-4,5,6,7-tetrahydro-1,2-benzisoxazole-6-carboxylic acid of melting point 162°–163° C.

EXAMPLE 48

5 g (0.012 mol) of methyl 3-(3,4-dichlorophenyl)-3a,5,6,7,8,8a-hexahydro-8a-pyrrolidino-4H-cyclohept[d]isoxazole-7-carboxylate were dissolved in a mixture of 5 ml of water, 5 ml of concentrated sulfuric acid and 5 ml of glacial acetic acid and heated at 120° C. for 1.5 hours. The mixture was cooled, whereupon the crystals which formed were filtered off and washed firstly with glacial acetic acid and then with water. After drying in a vacuum and crystallization from methanol, there was obtained 0.7 g of 3-(3,4-dichlorophenyl)-5,6,7,8-tetrahydro-4H-cyclohept[d]isoxazole-7-carboxylic acid of melting point 183°–185° C.

The starting material was prepared as follows:

(A) 8.5 g (0.05 mol) of methyl 3-oxocyclohexanecarboxylate were dissolved in 100 ml of dry toluene and 3.9 g (0.055 mol) of pyrrolidine were added followed by 0.01 g of p-toluenesulfonic acid. The mixture was heated under reflux for 5 hours in a Dean-Stark apparatus until no further water was collected. The toluene was removed by evaporation and the resulting enamine was dissolved in 50 ml of dry diethyl ether.

(B) 5.55 g (0.055 mol) of triethylamine were dissolved in 100 ml of dry diethyl ether and cooled to 0° C. A solution of 10.45 g (0.055 mol) of 3,4-dichlorobenzenecarboximidoyl N-hydroxy chloride in 100 ml of diethyl ether was added slowly while stirring over a period of 0.5 hour and stirring was continued for an additional 0.5 hour. The precipitated triethylamine hydrochloride was filtered off and washed with 50 ml of diethyl ether which was subsequently combined with the filtrate.

(C) The solutions obtained according to paragraph (A) and paragraph (B) were mixed together while stirring at 0°–5° C. and then stirred at 20° C. for 18 hours. The mixture was filtered and the filtrate was extracted with 300 ml of 2N hydrochloric acid. The aqueous-acidic solution was made basic with sodium carbonate and then extracted three times with 100 ml of diethyl ether each time. The combined ethereal extracts were washed once with sodium chloride solution, dried over magnesium sulfate and evaporated to give 13.7 g of methyl 3-(3,4-dichlorophenyl)-3a,5,6,7,8,8a-hexahydro-8a-pyrrolidino-4H-cyclohept[d]isoxazole-7-carboxylate; NMR: δ CDCl$_3$: 7.75–8.2 m (3H), 4.1 s (3H), 3.9–3.4 m (1H), 3–3.42 m (6H), 2.95–1.85 m (11H).

EXAMPLE 49

A solution of 3.4 g (0.02 mol) of methyl 3-oxocycloheptanecarboxylate, 1.91 g (0.022 mol) of morpholine and 0.005 g of p-toluenesulfonic acid in 30 ml of dry toluene was heated under reflux for 6 hours in a Dean-Stark apparatus until no additional water was collected. There were then added 2.02 g (0.02 mol) of triethylamine followed by a solution of 3.83 g (0.02.mol) of p-chlorobenzoyl chloride in 20 ml of toluene over a period of 10 minutes at 20° C. The mixture was heated at 60° C. for 6 hours, whereupon the precipitated triethylamine hydrochloride was removed from the cooled solution by filtration and washed with toluene. The combined toluene solutions were evaporated and 1.4 g (0.02 mol) of hydroxylamine hydrochloride dissolved in 10 ml of ethanol and 5 ml of pyridine were added. The mixture was heated under reflux for 2 hours. The solvent was removed by evaporation and an excess of 2N hydrochloric acid was added. The mixture was extracted twice with diethyl ether and the combined extracts were washed with 2N sodium carbonate solution and dried over magnesium sulfate. After evaporation, the resulting syrup was purified by column chromatography on silica gel using hexane/ethyl acetate (2:1) for the elution. There were obtained 1.2 g of methyl 3-(4-chlorophenyl)-5,6,7,8-tetrahydro-4H-cyclohept[c]isoxazole-7- -carboxylate of melting point 94°–95° C.

EXAMPLE 50

A suspension of 1.2 g of methyl 3-(4-chlorophenyl)-5,6,7,8-tetrahydro-4H-cyclohept[c]isoxazole-7-carboxylate in 15 ml of methanol, 3 ml of water and 0.5 g of potassium hydroxide was stirred for 16 hours, the resulting yellow solution was evaporated and the residue was dissolved in water. Acidification with 2N hydrochloric acid gave a white crystalline precipitate which was filtered off and dried. After crystallization from methanol, there was obtained 1 g of 3-(4-chlorophenyl)-5,6,7,8-tetrahydro-4H-cyclohept[c]isoxazole-7-carboxylic acid of melting point 231°–233° C.

EXAMPLE 51

5.7 g (0.0177 mol) of a mixture of methyl 3-(4-chlorophenyl)-3a,4,5,6,7,8,9,9a-octahydro[d]isoxazole-6-carboxylate and methyl 3-(4-chlorophenyl)-3a,4,5,6,7,8,9-,9a-octahydro[d]isoxazole-7-carboxylate were dissolved in 97 ml of glacial acetic acid. 1 ml of concentrated sulfuric acid was added followed by 3.54 g (0.0354 mol) of chromium trioxide and the mixture was stirred at 90° C. for 1.25 hours. The acetic acid was removed by evaporation and the residue was treated cautiously with water and 1N sodium carbonate solution until the mixture was basic. The mixture was then extracted four times with diethyl ether and the combined extracts were washed with sodium chloride solution and dried over magnesium sulfate. After evaporation, there were obtained 4 g of a mixture of methyl 3-(4-chlorophenyl)-4,5,6,7,8,9-hexahydrocyclooct [d]- isoxazole-7-carboxylate and methyl 3-(4-chlorophenyl)-4,5,6,7,8,9-hexahydrocyclooct[d]isoxazole-6-carboxylate in the form of a syrup. MS: m/e 320 (M+H)+.

The starting material was prepared as follows:

(A) 6.7 g (0.0663 mol) of triethylamine in 100 ml of diethyl ether were added at 0° C. over a period of 0.5 hour to a stirred solution of 12.54 g (0.066 mol) of 4-chlorobenzenecarboximidoyl N-hydroxy chloride in 150 ml of dry diethyl ether and stirring was continued for an additional 1 hour. The precipitated triethylamine hydrochloride was filtered off and washed with 75 ml of dry diethyl ether which was combined with the filtrate. The resulting solution was concentrated to half of the volume.

(B) The solution obtained according to paragraph (A) was cooled to 0°-5° C. and added to a solution of 10 g (0.6 mol) of methyl cyclooct-4-ene-carboxylate in 50 ml of dry diethyl ether while stirring. The mixture was stirred at −2° C. for 48 hours, the resulting precipitate was filtered off and the filtrate was evaporated. Purification of the resulting syrup by column chromatography on silica gel using hexane/ethyl acetate (4:1→1:1) for the elution gave 8 g of a mixture of methyl 3-(4-chlorophenyl)-3a,4,5,6,7,8,9,9a-octahydro[d]isoxazole-6-carboxylate and methyl 3-(4-chlorophenyl)-3a,4,5,6,7,8,9,9a-octahydro[d]isoxazole-7-carboxylate.

EXAMPLE 52

3 g (0.0094 mol) of a mixture of methyl 3-(4-chlorophenyl)-4,5,6,7,8,9-hexahydrocyclooct[d]isoxazole-6-carboxylate and methyl 3-(4-chlorophenyl)-4,5,6,7,8,9-hexahydrocyclooct[d]isoxazole-7-carboxylate were dissolved in 75 ml of methanol. 1.5 g of potassium hydroxide and 7 ml of water were added and the mixture was stirred at 20° C. for 18 hours. The methanol was removed by evaporation and an excess of water was added. The mixture was extracted twice with ethyl acetate and the aqueous phase was acidified with 2N hydrochloric acid. The aqueous-acidic layer was extracted three times with ethyl acetate and the combined ethyl acetate extracts were washed with sodium chloride solution and dried over magnesium sulfate. After evaporation and several crystallizations of the residue from ethyl acetate/hexane, there was obtained 0.78 g of 3-(4-chlorophenyl)-4,5,6,7,8,9-hexahydrocyclooct[d]isoxazole-7-carboxylic acid of melting point 147°-150° C.

EXAMPLE 53

1 g (0.003 mol) of methyl 3a,5,6,7,8,8a-hexahydro-3-(4-isopropylphenyl)-4H-cyclohept[d]isoxazole-6-carboxylate (diastereoisomer B) was dissolved in 30 ml of glacial acetic acid containing a few drops of concentrated sulfuric acid. The mixture was stirred and heated at 45° C., whereupon 0.79 g (0.0075 mol) of chromium trioxide was added and the heating was continued for 10 minutes. The acetic acid was removed by evaporation. The mixture was made basic with 2N sodium carbonate solution and extracted with ethyl acetate. Evaporation of the ethyl acetate extract and purification of the residue by column chromatography on silica gel using hexane/ethyl acetate (2:1) for the elution gave 0.408 g of methyl 5,6,7,8-tetrahydro-3-(4-isopropylphenyl)-4H-cyclohept[d]isoxazole-6-carboxylate; NMR: δ CDCl$_3$: 7.47 (m, 2H), 7.3 (m, 2H), 3.74 (s, 3H), 3.2 (m, 1H), 3.02-2.68 (m, 4H), 2.55 (m, 1H), 2.3-2.1 (m, 2H), 2.01-1.75 (m, 2H), 1.25 (d, 6H).

The starting material was prepared as follows:

4.04 g (0.04 mol) of triethylamine in 100 ml of dry diethyl ether were added slowly over a period of 0.5 hour to a solution of 7.88 g (0.04 mol) of 4-isopropylbenzenecarboximidoyl N-hydroxy chloride in 100 ml of dry diethyl ether while stirring at 5° C. and the stirring was continued for an additional 1 hour. The precipitated triethylamine hydrochloride was filtered off and washed with diethyl ether. The combined diethyl ether solutions were concentrated to a volume of less than 200 ml treated with a solution of 12.32 g (0.08 mol) of methyl cyclohept-4-enecarboxylate in 50 ml of diethyl ether at 5° C. and the mixture was stirred at 5° C. for 20 hours. 100 ml of hexane were added and the mixture was held at 5° C. to give white crystals of methyl 3a,5,6,7,8,8a-hexahydro-3-(4-isopropylphenyl)-4H-cyclohept[d]isoxazole-6-carboxylate (diastereoisomer A). Concentration of the mother liquors gave methyl 3a,5,6,7,8,8a-hexahydro-3-(4-isopropylphenyl)-4H-cyclohept[d]isoxazole-6-carboxylate (diastereoisomer B).

EXAMPLE 54

0.286 g (0.00091 mol) of methyl 5,6,7,8-tetrahydro-3-(4-isopropylphenyl)-4H-cyclohept[d]isoxazole-6-carboxylate was dissolved in 15 ml of methanol, 0.15 g (0.0027 mol) of potassium hydroxide and 2 ml of water were added and the mixture was stirred at 20° C. for 68 hours. The methanol was removed by evaporation. Water was added and the mixture was extracted once with diethyl ether. The aqueous layer was acidified with 2N hydrochloric acid and extracted with ethyl acetate. The extract was washed with sodium chloride solution and dried over magnesium sulfate. Evaporation gave a residue which was crystallized from methylcyclohexane to give 200 mg of 5,6,7,8-tetrahydro-3-(4-isopropylphenyl)-4H-cyclohept[d]isoxazole-6-carboxylic acid of melting point 109°-111° C.

EXAMPLE 55

3.06 g (0.01 mol) of methyl 3-(4-chlorophenyl)-5,6,7,8-tetrahydro-4H-cyclohept[d]isoxazole-6-carboxylate in 20 ml of dry tetrahydrofuran were added at −70° C. to a solution of lithium diisopropylamide prepared by adding 6 ml of a 2.5M solution of n-butyllithium in hexane over a period of 0.25 hour to a solution of 1.5 g (0.01015 mol) of diisopropylamine in 40 ml of tetrahydrofuran at −70° C. After stirring for 0.5 hour, 2.13 g (0.015 mol) of methyl iodide in 5 ml of tetrahydrofuran were added and the mixture was allowed to warm to 10° C. over a period of 0.5 hour. The mixture was added to ice/water and extracted three times with diethyl ether. The extracts were washed with sodium chloride solution to give 4.4 g of crude product which was purified by column chromatography on silica gel using hexane/diethyl ether for the elution. There were obtained 1.58 g of methyl 3-(4-chlorophenyl)-5,6,7,8-tetrahydro-6-methyl-4H-cyclohept[d]isoxazole-6-carboxylate; NMR: δ CDCl$_3$: 7.35 (m, 4H), 3.6 (s, 3H), 2.85 (m, 2H), 2.47 (m, 2H), 2.15 (m, 2H), 1.6 (m, 2H), 1.2 (3H).

EXAMPLE 56

1 g (3.12 mmol) of methyl 3-(4-chlorophenyl)-5,6,7,8-tetrahydro-6-methyl-4H-cyclohept[d]isoxazole-6-carboxylate was dissolved in 60 ml of methanol and a solution of 0.8 g of potassium hydroxide in 4 ml of water was added. The mixture was stirred at 20° C. for 48 hours and then at 50° C. for 6 hours. The methanol was removed by evaporation. Water was added and the mixture was acidified with 2N hydrochloric acid. The mixture was extracted three times with diethyl ether and the extracts were washed with sodium chloride solution and dried over magnesium sulfate. Evaporation and crystallization of the residue from ethyl acetate/hexane gave 0.594 g of 3-(4-chlorophenyl)-5,6,7,8-tetrahydro-6-methyl-4H-cyclohept[d]isoxazole-6-carboxylic acid of melting point 163° C.

EXAMPLE 57

3.38 g of methyl 3-(4-trifluoromethylphenyl)-3a,5,6,7,8,8a-hexahydro-8a-pyrrolidino-4H-cyclohept[d]isoxazole-7-carboxylate were dissolved in a mixture of 10 ml of glacial acetic acid, 10 ml of water and 10 ml of concentrated sulfuric acid and heated at 120° C. for 2 hours. The mixture was cooled, diluted with water and extracted three times with 100 ml of methylene chloride each time. The extracts were dried over magnesium sulfate and evaporated and the residue was crystallized from methanol to give 0.32 g of 3-(4-trifluoromethylphenyl)-5,6,7,8-tetrahydro-4H-cyclohept[d]isoxazole-7-carboxylic acid of melting point 222°–225° C.

The starting material was prepared as follows:

(A) A solution of 6.12 g (0.036 mol) of methyl 3-oxocycloheptanecarboxylate in 50 ml of dry toluene was treated with 3.3 ml (0.04 mol) of pyrrolidine and 0.01 g of p-toluenesulfonic acid. The mixture was heated in a Dean-Stark apparatus under reflux for 2 hours. The toluene was removed by evaporation and the resulting enamine was dissolved in 50 ml of dry diethyl ether.

(B) A solution of 4.04 g (0.04 mol) of triethylamine in 50 ml of dry diethyl ether was added slowly at 0° C. over a period of 0.5 hour to a solution of 8.94 g (0.04 mol) of 4-trifluoromethylbenzenecarboximidoyl N-hydroxy chloride in 100 ml of dry diethyl ether. The mixture was stirred at 0°–5° C. for 2 hours. The precipitated triethylamine hydrochloride was filtered off and washed with diethyl ether which was subsequently combined with the filtrate.

(C) The solutions obtained according to paragraphs (A) and (B) were mixed and held at 20° C. for 18 hours. The mixture was extracted with 2N hydrochloric acid and the combined aqueous solutions were made basic with 2N sodium carbonate solution and re-extracted with diethyl ether. The extracts were dried over magnesium sulfate and evaporated to give 3.38 g of methyl 3-(4-trifluoromethylphenyl)-3a,5,6,7,8,8 a-hexahydro-8a-pyrrolidino-4H-cyclohept[d]isoxazole-7-carboxylate in the form of a yellow gum; MS: m/e 410 (M)+.

EXAMPLE 58

2.32 g (0.006 mol) of methyl 3a,5,6,7,8,8a-hexahydro-3-(4-methoxyphenyl)-8a-pyrrolidino-4H-cyclohept[d]isoxazole-7-carboxylate were dissolved in a mixture of 6 ml of glacial acetic acid, 6 ml of water and 6 ml of concentrated sulfuric acid. The mixture was held at 100° C. for 1 hour, cooled and diluted with 20 ml of water to give a white precipitate which was filtered off, washed and dried. Crystallization from ethyl acetate gave 1.04 g of 5,6,7,8-tetrahydro-3-(4-methoxyphenyl)-4H-cyclohept[d]isoxazole-7-carboxylic acid of melting point 194°–196° C.

The starting material was prepared as follows:

(A) A solution of 7.65 g (0.045 mol) of methyl 3-oxocycloheptanecarboxylate, 4.17 ml (0.05 mol) of pyrrolidine and 0.01 g of p-toluenesulfonic acid in 50 ml of dry toluene was heated under reflux in a Dean-Stark apparatus until water was no longer collected. The solvent was removed by distillation to give the enamine which was dissolved in 50 ml of dry diethyl ether.

(B) 5.05 g (0.05 mol) of triethylamine in 50 ml of dry diethyl ether were added at 0° C. over a period of 0.25 hour while stirring to a solution of 9.25 g (0.05 mol) of 4-methoxybenzenecarboximidoyl N-hydroxy chloride in 50 ml of dry diethyl ether and the stirring was continued for an additional 1 hour. The precipitated triethylamine hydrochloride was filtered off and washed with diethyl ether which was subsequently combined with the filtrate.

(C) The solution prepared according to paragraph (A) and the solution prepared according to paragraph (B) were both cooled to 0° C., mixed and stirred at 20° C. for 16 hours. The mixture was extracted three times with 2N hydrochloric acid and the combined extracts were washed once with diethyl ether. The acidic solution was made basic with 2N sodium carbonate solution and extracted three times with diethyl ether. The extracts were washed once with sodium chloride solution and dried over magnesium sulfate. Evaporation of the solution and crystallization of the residue from methanol gave 3.4 g of methyl 3a,5,6,7,8,8a-hexahydro-3-(4-methoxyphenyl)-8a-pyrrolidino-4H-cyclohept[d]isoxazole-7-carboxylate in the form of a white solid.

EXAMPLE 59

6.12 g (0.0612 mol) of chromium trioxide were added to a solution of 6.99 g (0.023 mol) of methyl 3a,5,6,7,8,8a-hexahydro-3-(4-methoxyphenyl)-4H-cyclohept[d]isoxazole-6-carboxylate in 128 ml of acetic acid. The mixture was heated at 90° C. for 0.75 hour while stirring. Excess acetic acid was removed by evaporation. The mixture was treated with 2N sodium carbonate solution until basic and then extracted with diethyl ether. The extracts were dried over magnesium sulfate and evaporated to give, after crystallization from ethyl acetate/hexane, 1.7 g of methyl 5,6,7,8-tetrahydro-3-(4-methoxyphenyl)-4H-cyclohept[d]isoxazole-6-carboxylate of melting point 78°–81° C.

The starting material was prepared as follows:

4.04 g (0.04 mol) of triethylamine in 100 ml of dry diethyl ether were added at 5° C. over a period of 0.5 hour while stirring to a solution of 8.02 g (0.04 mol) of 4-methoxybenzenecarboximidoyl N-hydroxy chloride in 100 ml of dry diethyl ether and the stirring was continued for 0.5 hour. The precipitated triethylamine hydrochloride was filtered off, washed with diethyl ether and the combined ethereal solutions were concentrated to 200 ml. A solution of 12.32 g (0.08 mol) of methyl cyclohept-4-enecarboxylate in 100 ml of diethyl ether was added while cooling. The mixture was held at 5° C. overnight. 100 ml of hexane were added and the mixture was left at 5° C. for 24 hours. There were obtained 6.99 g of methyl 3a,5,6,7,8,8a-hexahydro-4-(4-methoxyphenyl)-4H-cyclohept[d]isoxazole-6-carboxylate in the form of a white crystalline precipitate; NMR: δ CDCl$_3$: 7.58–6.94 (4H), 4.85 (m, 1H), 3.8 (s,3H), 3.8 (m, 1H), 3.65 (d, 3H), 2.6–1.5 (m, 9H).

EXAMPLE 60

1.7 g (0.00565 mol) of methyl 5,6,7,8-tetrahydro-3-(4-methoxyphenyl)-4H-cyclohept[d]isoxazole-6-carboxylate were dissolved in 20 ml of methanol. 1 g of potassium hydroxide in 3 ml of water was added and the mixture was stirred at 20° C. for 66 hours. The methanol was removed by evaporation and an excess of water was added. The mixture was acidified with dilute hydrochloric acid and the resulting precipitate was filtered off, washed with water and dried. Crystallization from ethyl acetate/hexane gave 1.1 g of 5,6,7,8-tetrahydro-3-(4-methoxyphenyl)-4H-cyclohept[d]isoxazole-6-carboxylic acid of melting point 147°–148° C.

EXAMPLE 61

0.45 g (1.4 mmol) of a mixture of methyl cis- and trans-3-(4-chlorophenyl)-5,6,7,8-tetrahydro-8-methyl-4H-cyclohept[d]isoxazole-6-carboxylate in 5 ml of dry tetrahydrofuran was added at −78° C. to a solution of lithium diisopropylamide prepared by adding 0.8 ml (0.002 mol) of a 2.5M solution of n-butyllithium in hexane over a period of 0.5 hour to a solution of 0.28 ml (0.002 mol) of diisopropylamine in 5 ml of tetrahydrofuran at −78° C. and stirring for 0.5 hour. 0.092 ml (1.48 mmol) of methyl iodide was added at −78° C. and the mixture was stirred at a temperature up to 20° C. for 12 hours. The mixture was then treated with saturated ammonium chloride solution and extracted with dichloromethane. The extracts were dried over magnesium sulfate and evaporated to give 0.25 g of a mixture of methyl cis- and trans-3-(4-chlorophenyl)-5,6,7,8-tetrahydro-6,8-dimethyl-4H-cyclohept[d]isoxazole-6-carboxylate; NMR: δ CDCl$_3$: 7.45 (m, 4H), 3.75 (d, 3H), 3.13 (m, 1H), 2.57 (m, 2H), 2.25 (m, 2H), 1.3–1.9 (m, 8H).

EXAMPLE 62

600 mg (1.8 mmol) of a mixture of methyl cis- and trans-3-(4-chlorophenyl)-5,6,7,8-tetrahydro-6,8-dimethyl-4H-cyclohept[d]isoxazole-6-carboxylate were dissolved in 20 ml of methanol. A solution of 0.5 g of potassium hydroxide in 2 ml of water was added and the mixture was stirred at 50° C. for 72 hours. The methanol was removed by evaporation and water was added. The mixture was extracted once with diethyl ether and the aqueous layer was acidified with 2N hydrochloric acid and extracted three times with diethyl ether. The combined extracts were dried over magnesium sulfate and evaporated. Crystallization of the residue from ethyl acetate/hexane gave 170 mg of a mixture of cis- and trans-3-(4-chlorophenyl)-5,6,7,8-tetrahydro-6,8-dimethyl-4H-cyclohept[d]isoxazole-6-carboxylic acid of melting point 152°–154° C.

EXAMPLE 63

2.9 g (0.01 mol) of 3-(4-chlorophenyl)-5,6,7,8-tetrahydro-4H-cyclohept[d]isoxazole-6-carboxylic acid in 10 ml of dry tetrahydrofuran were added at −78° C. to a solution of lithium diisopropylamide prepared by adding 10 ml (0.025 mol) of a 2.5M solution of N-butyllithium in hexane over a period of 0.5 hour to a solution of 3.36 ml (0.023 mol) of diisopropylamine in 20 ml of tetrahydrofuran at −70° C. and stirring for 10 minutes. 0.684 ml (0.011 mol) of methyl iodide was added and the mixture was stirred for 6 hours at a temperature of up to 20° C. The mixture was acidified with 2N hydrochloric acid and extracted three times with diethyl ether. The extracts were dried over magnesium sulfate and evaporated. The residue was dissolved in 100 ml of 15% methanolic hydrogen chloride and the solution was heated under reflux for 48 hours. The methanol was removed by evaporation and the residue was taken up in diethyl ether. The solution was washed with 1M sodium carbonate solution and with sodium chloride solution and then dried over magnesium sulfate. The solution was evaporated and the residue was purified by column chromatography on silica gel using diethyl ether/hexane (1:1) for the elution to give 1.935 g of a mixture of methyl cis- and trans-3-(4-chlorophenyl)-5,6,7,8-tetrahydro-8-methyl-4H-cyclohept[d]isoxazole-6-carboxylate; NMR: δ CDCl$_3$: 7.44 (m, 4H), 3.75 (d, 3H), [3.43 m; 3.1–2.85 m; 2.8–2.65 m; 2.57–2.4 m; 2.25–2.0 m; 1.9–1.6 m] (8H), 1.44 (d, 3H).

EXAMPLE 64

A solution of 1 g of potassium hydroxide in 3 ml of water was added to a solution of 1.2 g (3.75 mmol) of a mixture of methyl cis- and trans-3-(4-chlorophenyl)-5,6,7,8-tetrahydro-8-methyl-4H-cyclohept[d]isoxazole-6-carboxylate in 40 ml of methanol. The mixture was heated under reflux for 12 hours. The methanol was removed by evaporation and water was added. The solution was extracted once with diethyl ether and the aqueous layer was acidified with 2N hydrochloric acid, then extracted three times with diethyl ether. The organic phase was dried over magnesium sulfate and evaporated. Recrystallization of the residue from ethyl acetate/hexane gave 800 mg of a mixture of cis- and trans-3-(4-chlorophenyl)-5,6,7,8-tetrahydro-8-methyl-4H-cyclohept[d]isoxazole-6-carboxylic acid of melting point 135°–138° C.

EXAMPLE 65

0.26 g (0.0013 mol) of 85% m-chloroperbenzoic acid was added to a solution of 0.25 g (0.00062 mol) of methyl exo-3-(4-chlorophenyl)-6-ethyl-3a,5,5a,6,6a,6b-hexahydro-6b-pyrrolidino-4H-cyclopropa[g]-1,2-benzisoxazole-6-carboxylate in 30 ml of chloroform and the mixture was stirred at 20° C. for 2 hours. An additional 0.13 g (0.00065 mol) of m-chloroperbenzoic acid was added and the stirring was continued for 2 hours. The chloroform was removed by evaporation and the residue was dissolved in 50 ml of ethyl acetate. The solution was washed three times with saturated sodium bicarbonate solution, once with 2N hydrochloric acid and once with sodium chloride solution. The solution was then dried over magnesium sulfate and evaporated to give 0.23 g of methyl exo-3-(4-chlorophenyl)-6-ethyl-5,5a,6,6a-tetrahydro-4H-cyclopropa[g]-1,2-benzisoxazole-6-carboxylate in the form of a syrup; NMR: δ CDCl$_3$: 7.65 (d, 2H), 7.45 (d, 2H), 3:75 (s, 3H), 3.5 (m, 1H), 2.8 (m, 2H), 2.55 (m, 1H), 2–2.35 (m, 2H), 1.2–1.7 (2H), 0.95 (t, 3H).

The starting material was prepared as follows:

(A) A solution of 6 g (0.0306 mol) of methyl endo/exo-7-ethyl-2-oxobicyclo[4.1.0]heptane-7-carboxylate (endo:exo ratio 2:3), 2.9 g (0.041 mol) of pyrrolidine and 0.01 g of p-toluenesulfonic acid in 100 ml of dry toluene was heated under reflux for 3 hours until water was no longer produced. The toluene was removed and replaced by 150 ml of dry diethyl ether.

(B) A solution of 3.4 g (0.0337 mol) of triethylamine in 100 ml of dry diethyl ether was added at 0° C. over a period of 0.75 hour while stirring to a solution of 6.39 g (0.034 mol) of 4-chlorobenzenecarboximidoyl N-hydroxy chloride in 100 ml of dry diethyl ether. After 1 hour, the precipitated triethylamine hydrochloride was filtered off and washed with 20 ml of dry diethyl ether which was subsequently combined with the filtrate.

(C) The solution prepared according to paragraph (B) was concentrated to half of the volume and added to the solution prepared according to paragraph (A) at 0°

C. The mixture was then stirred at 20° C. for 16 hours and then filtered. The filtrate was extracted three times with 2N hydrochloric acid. The aqueous-acidic solution was made basic with 2N sodium hydroxide solution and extracted with diethyl ether. After column chromatography on silica gel using hexane/diethyl ether (4:1) for the elution, there were firstly obtained 1.1 g of pure methyl endo-3-(4-chlorophenyl)-6-ethyl-3a,5,5a,6,6a,6b-hexahydro-6b-pyrrolidino-4H-cyclopropa[g]-1,2-benzisoxazole-6-carboxylate [MS: m/e 402 (M)+] and subsequently 0.60 g of pure methyl exo-3-(4-chlorophenyl)-6-ethyl-3a,5,5a,6,6a,6b-hexahydro-6b-pyrrolidino-4H-cyclopropa[g]-1,2-benzisoxazole-6-carboxylate, MS: m/e 402 (M)+.

EXAMPLE 66

In a manner analogous to that described in Example 65, from 0.592 g (0.0015.mol) of methyl endo-3-(4-chlorophenyl)-6-ethyl-3a,5,5a,6,6a,6b-hexahydro-6b-pyrrolidino-4H-cyclopropa[g]-1,2-benzisoxazole-6-carboxylate (prepared as described in Example 65) and 1.07 g (0.0053 mol) of m-chloroperbenzoic acid there was obtained 0.490 g of methyl endo-3-(4-chlorophenyl)-6-ethyl-5,5a,6,6a-tetrahydro-4H-cyclopropa[g]-1,2-benzisoxazole-6-carboxylate in the form of a syrup; NMR: δ CDCl$_3$: 7.65 (d, 2H), 7.45 (d, 2H), 3.7 (m, 1H), 3.53 (s, 3H), 2.65 (m, 1H), 2.4-2.2 (s, 2H), 2.05 (m, 1H), 1.8-1.2 (m, 3H), 1.05 (t, 3H).

EXAMPLE 67

0.23 g (0.00069 mol) of methyl exo-3-(4-chlorophenyl)-6-ethyl-5,5a,6,6a-tetrahydro-4H-cyclopropa[g]-1,2-benzisoxazole-6-carboxylate was stirred and heated at 80° C. for 1.3 hours in 12 ml of a mixture of equal volumes of glacial acetic acid, water and concentrated sulfuric acid. The mixture was cooled and treated with an excess of water. The mixture was then extracted twice with ethyl acetate, the extracts were washed with sodium chloride solution, dried over magnesium sulfate and evaporated. After recrystallization of the residue from ethyl acetate/hexane, there was obtained 0.064 g of exo-3-(4-chlorophenyl)-6-ethyl-5,5a,6,6a-tetrahydro-4H-cyclopropa[g]-1,2-benzisoxazole-6-carboxylic acid of melting point 215°-217° C.

EXAMPLE 68

0.255 g (0.00077 mol) of methyl endo-3-(4-chlorophenyl)-6-ethyl-5,5a,6,6a-tetrahydro-4H-cyclopropa[g]-1,2-benzisoxazole-6-carboxylate was heated under reflux for 18 hours with 5 ml of methanol, 2 drops of water and 0.16 g of potassium hydroxide. The methanol was removed by evaporation, an excess of water was added and the solution was extracted once with diethyl ether. The aqueous solution was then acidified with 2N hydrochloric acid and the solid which formed was filtered off, washed with water and dried. After crystallization from ethylacetate/hexane, there was obtained 0.150 g of endo-3-(4-chlorophenyl)-6-ethyl-5,5a,6,6a-tetrahydro-4H-cyclopropa[g]-1,2-benzisoxazole-6-carboxylic acid of melting point 168°-170° C. (decomposition).

EXAMPLE 69

7 0.38 .g (1.2 mmol) of methyl endo-3-(4-chlorophenyl)-3a,4,5,5a,6a,6b-hexahydro-6-methyl-4H-cyclopropa[g]-1,2-benzisoxazole-6-carboxylate was combined with 0.36 g (3.6 mmol) of chromium trioxide in 30 ml of glacial acetic acid containing 2 drops of concentrated sulfuric acid. The mixture was heated at 100° C. for 1 hour and the acetic acid was then removed by evaporation under reduced pressure. The residue was purified by chromatography on silica gel using diethyl ether/hexane (1:2) for the elution. There was obtained 0.1 g of methyl endo-3-(4-chlorophenyl)-5,5a,6,6a-tetrahydro-6-methyl-4H-cyclopropa[g]-1,2-benzisoxazole-6-carboxylate; NMR: δ CDCl$_3$: 7.65 (m, 2H), 7.40 (m, 2H), 3.55 (s, 3H), 2.7 (m, 1H), 2.45 (m, 1H), 2.3 (m, 2H), 2.1 (m, 1H), 1.8 (m, 1H), 1.5 (s, 3H).

The starting material was prepared as follows:

(A) 5.66 g (33.3 mmol) of silver nitrate were added to 5.89-g (27 mmol) of endo-8-bromo-8-methylbicyclo[4.2:0]oct-2-en-7-one (prepared as described in Example 71) in 120 ml of methanol and the mixture was heated under reflux for 2 hours. Sodium chloride solution was added. The mixture was filtered and the filtrate was evaporated. The residue was taken up in diethyl ether and washed in sequence with aqueous sodium bicarbonate solution and sodium chloride solution and then dried over magnesium sulfate. Removal of the solvent gave 2.85 g of (1α,6α,7β)methylbicyclo[4:1:0-]hept-2-ene-7-methyl-7-carboxylate.

(B) A solution of 4.04 g (40 mmol) of triethylamine in 110 ml of hexane was added at 5° C. over a period of 0.5 hour while stirring to a solution of 8.2 g (40 mmol) of 4-chlorobenzenecarboximidoyl N-hydroxy chloride in 110 ml of dry diethyl ether. After 1 hour, the precipitated triethylamine hydrochloride was filtered off and washed with 20 ml of dry diethyl ether which was subsequently combined with the filtrate.

(C) The solution prepared according to paragraph (B) was added to 7.18 g (40 mmol) of the compound prepared according to paragraph (A). The mixture was stirred at room temperature and, after 16 hours, a second equivalent of the solution prepared according to paragraph (B, was added to the mixture. After 18 hours, the mixture was filtered and the crude product was chromatographed on silica gel using diethyl ether/hexane (1:2) for the elution. There were firstly obtained 1.06 g of methyl endo-3-(4-chlorophenyl)-3a,4,5,5a,-6a,6b-hexahydro-6-methyl- 4H-cyclopropa[g]-1,2-benzisoxazole-6-carboxylate; NMR: δ CDCl$_3$: 7.65 (m, 2H), 7.35 (m, 2H), 4.8 (d, 1H), 3.7 (s, 3H), 3.55 (m, 1H), 2.05 (m, 1H), 1.75 (m, 1H), 1.55 (m, 2H), 1.35 (s, 3H), 1.3 (m, 1H), 1.1 (m, 1H).

EXAMPLE 70

· 0.285 g (0.9 mmol) of methyl endo-3-(4-chlorophenyl)-5,5a,6,6a-tetrahydro-6-methyl-4H-cyclopropa[g]-1,2-benzisoxazole-6-carboxylate was treated with 10 ml of methanol and 0.15 g of potassium hydroxide in 1 ml of water. The mixture was heated under reflux for 16 hours and the methanol was removed by evaporation. Acidification with 2N hydrochloric acid gave 0.21 g of endo-3-(4-chlorophenyl)-5,5a,6,6a-tetrahydro-6-methyl-4H-cyclopropa[g]-1,2-benzisoxazole-6-carboxylic acid of melting point 194°-197° C.

EXAMPLE 71

0.38 g (0.2 mmol) of methyl exo-3-(4-chlorophenyl)-3a,4,5,5a,6a,6b-hexahydro-6-methyl-4H-cyclopropa[g]-1,2-benzisoxazole-6-carboxylate was combined with 0.36 g (3.6 mmol) of chromium trioxide in 30 ml of glacial acetic acid containing 2 drops of concentrated sulfuric acid. The mixture was heated at 100° C. for 1 hour and the acetic acid was then removed by evaporation under reduced pressure. The residue was purified by chromatography on silica gel using diethyl ether/hexane (1:2) for the elution. There was obtained 0.18 g of methyl exo-3-(4-chlorophenyl)-5,5a,6,6a-tetrahydro-6-methyl-4H-cyclopropa[g]-1,2-benzisoxazole-6-carboxylate; NMR: δ CDCl$_3$: 7.65 (m, 2H), 7.45 (m, 2H), 3.75 (s, 3H), 2.8 (m, 2H), 2.5 (m, 1H), 2.2 (m, 2H), 2.0 (m, 1H), 1.15 (s, 3H).

The starting material was prepared as follows:

(A) 81.3 g (0.38 mol) of 2-bromopropionyl bromide in 100 ml of hexane were added over a period of 1 hour to 39.8 g (0.5 mol) of 1,3-cyclohexadiene and 38.6 g (0.38 mol) of triethylamine while maintaining the temperature below 40° C. by occasional cooling. After an additional 3 hours at room temperature the precipitated triethylamine hydrobromide was removed by filtration. The filtrate was evaporated and the residue was purified by distillation under reduced pressure and subsequently by chromatography on silica gel using 4% diethyl ether in hexane for the elution. There were obtained 9.48 g of exo-8-bromo-8-methylbicyclo[4:2:0]oct-2-en-7-one and 5 89 g of endo-8-bromo-8-methylbicyclo[4:2:0]oct-2-en-7-one.

(B) 15.7 g (93 mmol) of silver nitrate were added to 15.85 g (74 mmol) of exo-8-bromo-8-methylbicyclo[4:2:-0]oct-2-en-7-one in 320 ml of methanol and the mixture was heated under reflux for 3 hours. Sodium chloride solution was then added and the mixture was filtered. The filtrate was evaporated and the resulting oil was taken up in diethyl ether. The ethereal solution was washed repeatedly with aqueous sodium bicarbonate solution and sodium chloride solution and then died over magnesium sulfate. Removal of the solvent gave 10 g of (1α,6α7α)-methylbicyclo[4:1:0]hept-2-ene-7-methyl-7-carboxylate.

(C) A solution of 6.08 g (60 mmol) of triethylamine in 150 ml of hexane was added at 5° C. over a period of 30 minutes while stirring to a solution of 11.39 g (60 mmol) of 4-chlorobenzenecarboximidoyl N-hydroxy chloride in 150 ml of dry diethyl ether. After 1 hour, the precipitated triethylamine hydrochloride was filtered off and washed with 20 ml of dry diethyl ether which was subsequently combined with the filtrate.

(D) The solution prepared according to paragraph (C) was added to 10 g (60 mmol) of the compound obtained according to paragraph (B).and the mixture was stirred. After 16 hours, a second equivalent of the solution prepared according to paragraph (C) was filtered and the filtrate was added to the mixture. After 18 hours, the mixture was filtered and the crude product was purified by chromatography on silica gel using diethyl ether/hexane (1:2) for the elution. After twofold recrystallization of the Product from methanol, there was obtained 0.48 g of methyl exo-3-(4-chlorophenyl)-3a,4,5,5a,6a,6b-hexahydro-6-methyl-4H-cyclopropa[g]-1,2-benzisoxazole-6-carboxylate; NMR: δ CDCl$_3$: 7.65 (m, 2H), 7.4 (m, 2H), 4.5 (d, 1H), 3.7 (s, 3H), 3.0 (m, 1H), 2.15 (m, 2H), 1.95 (m, 1H), 1.8 (m, 1H), 1.2 (m, 5H).

EXAMPLE 72

0.285 g (0.9 mmol) of methyl exo-3-(4-chlorophenyl)-5,5a,6,6a-tetrahydro-6-methyl-4H-cyclopropa[g]-1,2-benzisoxazole-6-carboxylate was treated with 8 ml of methanol and 0.15 g of potassium hydroxide in 1 ml of water. The solution was heated at 50° C. for 3 hours. The methanol was removed by evaporation and, after acidification with 2N hydrochloric acid, there was obtained 0.13 g of exo-3-(4-chlorophenyl)-5,5a,6,6a-tetrahydro-6-methyl-4H-cyclopropa[g]-1,2-benzisoxazole-6-carboxylic acid of melting point 230° C.

EXAMPLE 73

0.57 g (1.48 mmol) of a cis/trans mixture of methyl 4-bromo-3-(4-chlorophenyl)-5,6,7,8-tetrahydro-4H-cyclohept[d]isoxazole-7-carboxylate (prepared as described in Example 9) in 10 ml of dry dimethylformamide was stirred at room temperature for 16 hours with 0.3 g (6.1 mmol) of sodium cyanide. 100 ml of water were added and the mixture was extracted four times with dichloromethane. The combined organic phases were dried over magnesium sulfate and evaporated, and the residue was chromatographed on silica gel using dichloromethane for the elution. There was obtained 0.1 g of methyl cis- and trans-3-(4-chlorophenyl)-4-cyano-5,6,7,8-tetrahydro-4H-cyclohept[d]isoxazole-7-carboxylate in a ratio of about 1:1; melting point 114°–115° C.

EXAMPLE 74

0.1 g (0.185 mol) of a mixture of methyl cis- and trans-3-(4-chlorophenyl)-4-cyano-5,6,7,8-tetrahydro-4H-cyclohept[d]isoxazole-7-carboxylate (cis/trans ratio 1:1) was stirred in 10 ml of dioxane and 2 ml of 1N aqueous sodium hydroxide solution were added. The mixture was stirred at room temperature for 1 hour, 30 ml of water were then added and the solution was partially evaporated. The solution was acidified with 1N hydrochloric acid and the precipitate was collected, washed with water and dried. Recrystallization of the residue from acetonitrile yielded 0.08 g of cis-3-(4-chlorophenyl)-4-cyano-5,6,7,8-tetrahydro-4H-cyclohept[d]isoxazole-7-carboxylic acid of melting point 263° C. (decomposition).

EXAMPLE 75

0.5 g (1.3 mmol) of a cis/trans mixture of methyl 4-bromo-3-(4-chlorophenyl)-5,6,7,8-tetrahydro-4H-cyclohept[d]isoxazole-7-carboxylate (prepared as described in Example 9) in 5 ml of dry dimethylformamide was stirred, cooled in ice and treated with 0.15 g (2.1 mmol) of sodium methanethiolate. The mixture was stirred at room temperature for 24 hours and then evaporated. The residue was partitioned between water and dichloromethane and the organic phase was dried over magnesium sulfate and evaporated. The residue was chromatographed on silica gel using dichloromethane for the elution and there were obtained 0.028 g of methyl cis-3-(4-chlorophenyl)-5,6,7,8-tetrahydro-4-methylthio-4H-cyclohept[d]isoxazole-7-carboxylate of melting point 110°–112° C. and 0.041 g of methyl trans-3-(4-chlorophenyl)-5,6,7,8-tetrahydro-4-methylthio-4H-cyclohept[d]isoxazole-7-carboxylate of melting point 127°–128° C.

EXAMPLE 76

0.037 g (0.105 mmol) of methyl trans-3-(4-chlorophenyl)-5,6,7,8-tetrahydro-4-methylthio-4H-cyclohept[d]isoxazole-7-carboxylate was stirred in 5 ml of dioxane and 2 ml of 1N aqueous sodium hydroxide solution were added. The mixture was stirred at room temperature for 1 hour, then diluted with water and partially evaporated. Water was added and the resulting solution was acidified with 1N hydrochloric acid. The precipitate was collected, washed with water and dried to give, after recrystallization from ethyl acetate/hexane, 0.0237 g of trans-3-(4-chlorophenyl)-5,6,7,8-tetrahydro-4-methylthio-4H-cyclohept[d]isoxazole-7-carboxylic acid of melting point 177°-178° C.

EXAMPLE 77

0.024 g (0.068 mmol) of methyl cis-3-(4-chlorophenyl)-5,6,7,8-tetrahydro-4-methylthio-4H-cyclohept[d]isoxazole-7-carboxylate was stirred in 5 ml of dioxane and 2 ml of 1N aqueous sodium hydroxide solution were added. The mixture was stirred at room temperature for 1 hour. Water was then added and the solution was partially evaporated. The aqueous solution was acidified with 1N hydrochloric acid and the precipitate was collected, washed with water and dried to give 0.0146 g of cis-3-(4-chlorophenyl)-5,6,7,8-tetrahydro-4-methylthio-4H-cyclohept[d]isoxazole7-carboxylic acid of melting point 241°-242° C.

EXAMPLE 78

1 g (3.13 mmol) of methyl 3-(4-chlorophenyl)-5,6,7,8-tetrahydro-4-methylene-4H-cyclohept[d]isoxazole-7-carboxylate was dissolved in 60 ml of glacial acetic acid and 0.3 g of 5% platinum-on-carbon catalyst was added under a nitrogen atmosphere. The mixture was shaken in a hydrogen atmosphere at room temperature and under atmospheric pressure for 8 hours. The catalyst was removed by filtration and washed with glacial acetic acid. The filtrate was evaporated and the residue was chromatographed on silica gel using 20% ethyl acetate in hexane for the elution. There were obtained 0.47 g of methyl cis-3-(4-chlorophenyl)-5,6,7,8-tetrahydro-4-methyl-4H-cyclohept[d]isoxazole-7-carboxylate of melting point 90°-91° C. and 0.45 g of methyl trans-3-(4-chlorophenyl)-5,6,7,8-tetrahydro-4-methyl-4H-cyclohept[d]isoxazole-7-carboxylate of melting point 108° C.

The starting material was prepared as follows:

(A) 1 g (2.6 mmol) of a cis/trans mixture of methyl 4-bromo-3-(4-chlorophenyl)-5,6,7,8-tetrahydro-4H-cyclohept[d]isoxazole-7-carboxylate (prepared as described in Example 9) was dissolved in 30 ml of dioxane and 3 ml of water were added. The solution was held at room temperature for 24 hours and then evaporated to a low volume. Water was added and the mixture was extracted three times with dichloromethane. The combined organic phases were dried over magnesium sulfate and evaporated. The residue was chromatographed on silica gel using dichloromethane and subsequently ethyl acetate for the elution. There was obtained 0.3 g of a cis/trans mixture of methyl 3-(4-chlorophenyl)-5,6,7,8-tetrahydro-4-hydroxy-4H-cyclohept[d]isoxazole-7-carboxylate in the form of a white solid.

(B) 2.4 g (7.5 mmol) of a cis/trans mixture of methyl 3-(4-chlorophenyl)-5,6,7,8-tetrahydro-4-hydroxy-4H-cyclohept[d]isoxazole-7-carboxylate were stirred in 150 ml of acetone and Jones' reagent was added dropwise until the orange color persisted for 20 minutes. The mixture was filtered and the residue was washed with acetone. The combined filtrate and washings were treated with isopropanol and the mixture was neutralized by stirring with solid sodium bicarbonate. The mixture was filtered. The filtrate was evaporated and the residue was partitioned between dichloromethane and water. The organic phase was dried over magnesium sulfate and evaporated. The residue was treated with hexane and the resulting solid was collected and dried to give 1.85 g of methyl 3-(4-chlorophenyl)-5,6,7,8-tetrahydro-4-oxo-4H-cyclohept[d]isoxazole-7-carboxylate of melting point 108°-109° C.

(C) 2.65 g of a mixture of methyltriphenylphosphonium bromide and sodium amide (approximately 6.3 mmol of each component) was stirred under nitrogen and 16 ml of dry tetrahydrofuran were added. After stirring at room temperature for 15 minutes, the mixture was cooled in ice and a solution of 1.85 g (5.79 mmol) of methyl 3-(4-chlorophenyl)-5,6,7,8-tetrahydro-4-oxo-4H-cyclohept[d]isoxazole-7-carboxylate in 11 ml of dry tetrahydrofuran was added dropwise. The mixture was stirred in the cold for 0.5 hour and then at room temperature for 3 hours. The mixture was treated with 10 ml of saturated aqueous ammonium chloride solution and then partially evaporated. The aqueous phase was extracted three-times with dichloromethane and the combined organic phases were dried over magnesium sulfate and evaporated. The residue was triturated with diethyl ether. The solid was filtered off and washed with diethyl ether and the filtrate was evaporated. The residue was chromatographed on silica gel using 50% ethyl acetate/hexane for the elution. There were obtained 1.06 g of methyl 3-(4-chlorophenyl)-5,6,7,8-tetrahydro-4-methylene-4H-cyclohept[d]isoxazole-7-carboxylate of melting point 113°-114° C.

EXAMPLE 79

0.079 g (0.25 mmol) of methyl cis-3-(4-chlorophenyl)-5,6,7,8-tetrahydro-4-methyl-4H-cyclohept[d]isoxazole-7-carboxylate in 10 ml of dioxane was stirred at room temperature for 1 hour with 5 ml of 1N aqueous sodium hydroxide solution. Water was added and the solution was partially evaporated. The solution was acidified with 1N hydrochloric acid and the precipitate was collected, washed with water and dried to give 0.065 g of cis-3-(4-chlorophenyl)-5,6,7,8-tetrahydro-4-methyl-4H-cyclohept[d]isoxazole-7-carboxylic acid of melting point 213° C.

EXAMPLE 80

0.36 g (1.13 mmol) of methyl trans-3-(4-chlorophenyl)-5,6,7,8-tetrahydro-4-methyl-4H-cyclohept[d]isoxazole-7-carboxylate in 35 ml of dioxane was stirred at room temperature for 1 hour with 15 ml of 1N aqueous sodium hydroxide solution. Water was added and the solution was partially evaporated. Additional water was added to give a solution which was then acidified with 1N hydrochloric acid. The precipitate was filtered off, washed with water and dried to give 0.278 g of trans-3-(4-chlorophenyl)-5,6,7,8-tetrahydro-4-methyl-4H-cyclohept[d]isoxazole-7-carboxylic acid of melting point 154°-155° C.

EXAMPLE 81

2 g (0.0047 mol) of ethyl endo-3-(3,4-dichlorophenyl)-3a,5,5a,6,6a,6b-hexahydro-6b-pyrrolidino-4H-cyclopropa[g]-1,2-benzisoxazole-6-carboxylate in 5 ml of concentrated sulfuric acid, 5 ml of glacial acetic acid and 5 ml of water was heated at 150° C. for 2 hours. The crystals which were obtained upon cooling were filtered off, washed with water and dried in a vacuum. The crude product was recrystallized from ethyl acetate/hexane and there was obtained 0.30 g of endo-3-(3,4-dichlorophenyl)-5,5a,6,6a-tetrahydro-4H-cyclopropa[g]-1,2-benzisoxazole-6-carboxylic acid of melting point 208° C.

The starting material was prepared as follows:

(A) A solution of 4 g (22 mmol) of ethyl endo/exo-2-oxobicyclo[4.1.0]heptanecarboxylate (endo:exo ratio 1:1) and 4.77 g (67 mmol) of pyrrolidine in 50 ml of dry benzene was heated under reflux for 3 hours until water was no longer produced. The benzene was removed and replaced by 30 ml of dry diethyl ether.

(B) A solution of 2.26 g (22 mmol) of triethylamine in 10 ml of dry diethyl ether was added at 5° C. over a period of 15 minutes while stirring to a solution of 4.94 g (22 mmol) of 3,4-dichlorobenzenecarboximidoyl N-hydroxy chloride in 20 ml of dry diethyl ether. After 1 hour, the precipitated triethylamine hydrochloride was filtered off and washed with 20 ml of dry diethyl ether which was subsequently combined with the filtrate.

(C) The solution prepared according to paragraph (B) was added to the solution prepared according to paragraph (A). After 5 hours, the mixture was filtered and the solvent was removed under reduced pressure. The residue was subjected to column chromatography on silica gel using ethyl acetate/hexane (1:1) for the elution. There were firstly obtained 2 g of ethyl endo-3-(3,4-dichlorophenyl)-3a,5,5a,6,6a,6b-hexahydro-6b-pyrrolidino-4H-cyclopropa[g]-1,2- -benzisoxazole-6-carboxylate; NMR: δ CDCl$_3$: 7.82 (d, 1H), 7.62 (dd, 1H), 7.47 (d, 1H), 4.08 (m, 2H), 3.18 (dd, 1H), 2.75 (br, s, 4H), 2.40 (m, 1H), 1.95 (m, 5H), 1.63 (m, 4H), 1.30 (t, 3H), 1.08 (m, 1H). There was subsequently eluted 1 g of ethyl exo-3-(3,4-dichlorophenyl)-3a,5,5a,6,6a,6b-hexahydro-6b-pyrrolidino-4H-cyclopropa[g]-1,2-benzisoxazole-6-carboxylate; NMR: δ CDCl$_3$: 7.7 (m, 1H), 7.48 (m, 2H), 4.18 (m, 2H), 3.36 (m, 1H), 2.88 (m, 4H), 2.17 (dd, 1H), 2.01-1.55 (m, 10H), 1.32 (t, 3H).

EXAMPLE 82

1 g of ethyl exo-3-(3,4-dichlorophenyl)-3a,5,5a,6,6a,6b-hexahydro-6b-pyrrolidino-4H-cyclopropa[g]-1,2-benzisoxazole-6-carboxylate was treated with a mixture of concentrated sulfuric acid, glacial acetic acid and water in a manner analogous to that described in Example 81. The crude product was recrystallized from methanol to give 0.24 g of exo-3-(3,4-dichlorophenyl)-5,5a,6,6a-tetrahydro-4H-cyclopropa[g]-1,2-benzisoxazole-6-carboxylic acid of melting point 232° C.

EXAMPLE 83

1.5 g of ethyl endo-3-(4-methoxyphenyl)-3a,5,5a,6,6a,6b-hexahydro-6b-pyrrolidino-4H-cyclopropa[g]1,2-benzisoxazole-6-carboxylate were treated with a mixture of concentrated sulfuric acid, glacial acetic acid and water in a manner analogous to that described in Example 81. The crude product was recrystallized from ethyl acetate and there was obtained 0.135 g of endo-3-(4-methoxyphenyl)-5,5a,6,6a-tetrahydro-4H-cyclopropa[g]-1,2-benzisoxazole-6-carboxylic acid of melting point 176° C.

The starting material was prepared as follows:

(A) A solution of 4 g (22 mmol) of ethyl endo/exo-2-oxobicyclo[4:1:0]heptanecarboxylate (endo:exo ratio 1:1) and 4.77 g (67 mmol) of pyrrolidine in 50 ml of dry benzene was heated under reflux for 3 hours until water was no longer produced. The benzene was removed and replaced by 30 ml of dry diethyl ether.

(B) A solution of 2.26 g (22 mmol) of triethylamine in 10 ml of dry diethyl ether was added at 5° C. over a period of 0.25 hour while stirring to a solution of 4.07 g (22 mmol) of 4-methoxybenzenecarboximidoyl N-hydroxy chloride in 20 ml of dry diethyl ether. After 1 hour, the precipitated triethylamine hydrochloride was filtered off and washed with 20 ml of dry diethyl ether which was subsequently combined with the filtrate.

(C) The solution prepared according to paragraph (B) was added to the solution prepared according to paragraph (A). After 14 hours, the mixture was filtered and the filtrate was extracted three times with 2N hydrochloric acid each time. The combined aqueous-acidic extracts were made basic with 2N sodium carbonate solution and extracted with diethyl ether. After chromatography on silica gel using ethyl acetate/hexane (1:1) for the elution, there were firstly obtained 1.5 g of ethyl endo-3-(4-methoxyphenyl)-3a,5,5a,6,6a,6b-hexahydro-6b-pyrrolidino-4H-cyclopropa[g]-1,2-benzisoxazole-6-carboxylate; NMR: δ CDCl$_3$: 7.7 (m, 2H), 6.93 (m, 2H), 4.10 (m, 2H), 3.85 (s, 3H), 3.21 (m, 1H), 2.76 (br, s, 4H), 2.42 (m, 1H), 2.04 (m, 2H), 1.90 (m, 2H), 1.61 m, 6H), 1.29 (t, 3H). There were subsequently eluted 1.5 g of ethyl exo-3-(4-methoxyphenyl)-3a,5,5a,6,6a,6b-hexahydro-6b-pyrrolidino-4H-cyclopropa[g]-1,2-benzisoxazole-6-carboxylate; NMR: δ CDCl$_3$: 7.55 (m, 2H), 6.95 (m, 2H), 4.18 (m, 2H), 3.85 (s, 3H), 3.36 (m, 1H), 2.86 (m, 4H), 2.16 (dd, 1H), 1.94 (m, 2H), 1.79 (m, 4H), 1.64 (m, 4H), 1.30 (s, 3H).

EXAMPLE 84

1.5 g of ethyl exo-3-(4-methoxyphenyl)-3a,5,5a,6,6a,6b-hexahydro-6b-pyrrolidino-4H-cyclopropa[g]-1,2-benzisoxazole-6-carboxylate were treated with a mixture of concentrated sulfuric acid, glacial acetic acid and water in a manner analogous to that described in Example 81. The crude product was recrystallized from methanol/ethanol to give 0.15 g of exo-3-(4-methoxyphenyl)-5,5a,6,6a-tetrahydro-4H-cyclopropa[g]-1,2-benzisoxazole-6-carboxylic acid of melting point 237° C.

EXAMPLE 85

1.8 g (8.8 mmol) of m-chloroperbenzoic acid in 20 ml of chloroform were added over a period of 5 minutes to a solution of 3.0 g (8.1 mmol) of ethyl endo-3-(4-fluorophenyl)-3a,5,5a,6,6a,6b-hexahydro-6b-pyrrolidino-4H-cyclopropa[ g]-1,2-benzisoxazole-6-carboxylate in 10 ml of chloroform. After 6 hours, the m-chlorobenzoic acid was removed by filtration and the filtrate was washed with sodium bicarbonate solution. The solvent was removed by evaporation and the resulting crude ethyl endo-3-(4-fluorophenyl)-3a,5,5a,6,6a,6b-hexahydro-6b-(N-oxido-1-pyrrolidinyl)-4H-cyclopropa[g]-1,2-benzisoxazole-6-carboxylate was heated at 120° C. in an oil bath. There were thus obtained 2.3 g of ethyl endo-3-(4-fluorophenyl)-5,5a,6,6a-tetrahydro-4H-cyclopropa[g]-1,2-benzisoxazole-6-carboxylate of melting point 81°-82° C.

The starting material was prepared as follows:

(A) A solution of 4 g (22 mmol) of ethyl endo/exo-2-oxobicyclo[4:1:0]heptanecarboxylate (endo:exo ratio 1:1) and 4.77 g (67 mmol) of pyrrolidine in 50 ml of dry benzene was heated under reflux for 3 hours until water was no longer produced. The benzene was removed and replaced by 30 ml of dry diethyl ether.

(B) A solution of 2.26 g (22 mmol) of triethylamine in 10 ml of dry diethyl ether was added at 5° C. over a period of 0.25 hour while stirring to a solution of 3.82 g (22 mmol) of 4-fluorobenzenecarboximidoyl N-hydroxy chloride in 20 ml of dry diethyl ether. After 1 hour, the precipitated triethylamine hydrochloride was filtered off and washed with 20 ml of dry diethyl ether which was subsequently combined with the filtrate.

(C) The solution prepared according to paragraph (B) was added to the solution prepared according to paragraph (A). After 14 hours, the mixture was filtered and the filtrate was extracted three times with 2N hydrochloric acid each time. The combined aqueous-acidic extracts were made basic with 2N sodium carbonate solution and extracted with diethyl ether. After chromatography on silica gel using ethyl acetate/hexane (1:1) for the elution, there were firstly obtained 3 g of ethyl endo-3-(4-fluorophenyl)-3a,5 5a,6,6a,6b-hexahydro-6b-pyrrolidino-4H-cyclopropa[g]-1,2-benzisoxazole-6-carboxylate [MS: m/e 372 (M)+] and subsequently 1.8 g of ethyl exo-3-(4-fluorophenyl)-3a,5,5a,6-,6a,6b-hexahydro-6b-pyrrolidino-4H-cyclopropa[g]-1,2-benzisoxazole-6-carboxylate; MS: m/e 372 (M)+.

EXAMPLE 86

2.3 g of ethyl endo-3-(4-fluorophenyl)-5,5a,6,6a,-tetrahydro-4H-cyclopropa[g]-1,2-benzisoxazole-6-carboxylate were heated under reflux for 4 hours with 3.2 g of sodium hydroxide in 15 ml of water and 200 ml of methanol. Acidification with 2N hydrochloric acid and recrystallization from methanol gave 1.7 g of endo-3-(4-fluorophenyl)-5,5a,6,6a-tetrahydro-4H-cyclopropa[g]-1,2-benzisoxazole-6-carboxylic acid of melting point 174° C.

EXAMPLE 87

0.27 g (1.34 mmol) of m-chloroperbenzoic acid in 10 ml of chloroform was added over a period of 5 minutes to a solution of 0.5 g (1.34 mmol) of exo-3-(4-fluorophenyl)-3a,5,5a,6,6a,6b-hexahydro-6b-pyrrolidino-4H-cyclopropa[g]-1,2-benzisoxazole-6-carboxylate in 5 ml of chloroform. After 5 hours, the m-chlorobenzoic acid was removed by filtration and the filtrate was washed with dilute sodium bicarbonate solution. The solvent was removed and the resulting crude ethyl exo-3-(4-fluorophenyl)-3a,5,5a,6,6a,6b-hexahydro-6b-(N-oxido-1-pyrrolidinyl)-4H-cyclopropa[g]-1,2-benzisoxazole-6-carboxylate was heated at 120° C. in an oil bath. There was thus obtained 0.39 g of ethyl exo-3-(4-fluorophenyl)-5,5a,6,6a-tetrahydro-4H-cyclopropa[g]-1,2-benzisoxazole-6-carboxylate of melting point 122°–123° C.

EXAMPLE 88

0.39 g of ethyl exo-3-(4-fluorophenyl)-5,5a,6,6a-tetrahydro-4H-cyclopropa[g]-1,2-benzisoxazole-6-carboxylate was heated under reflux for 2 hours with 0.54 g of sodium hydroxide in 2 ml of water and 20 ml of methanol. Acidification with 2N hydrochloric acid and recrystallization from methanol gave 0.34 g of exo-3-(4-fluorophenyl)-5,5a,6,6a-tetrahydro-4H-cyclopropa[g]-1,2-benzisoxazole-6-carboxylic acid of melting point 251° C.

EXAMPLE 89

1.5 g (7.4 mmol) of m-chloroperbenzoic acid in 20 ml of chloroform were added over a period of 5 minutes to a solution of 3.0 g (7.1 mmol) of ethyl endo-3-(4-trifluoromethylphenyl)-3a,5,5a,6,6a,6b-hexahydro-6b-pyrrolidino-4H-cyclopropa[g]-1,2-benzisoxazole-6-carboxylate in 10 ml of chloroform. After 16 hours, the m-chlorobenzoic acid was removed by filtration and the filtrate was washed with dilute sodium bicarbonate solution. The solvent was removed and the resulting crude ethyl endo-3-(4-trifluoromethylphenyl)-3a,5,5a,6-,6a,6b-hexahydro-6b-(N-oxido-1-pyrrolidinyl)-4H-cyclopropa[g]-1,2-benzisoxazole-6-carboxylate was heated at 120° C. in an oil bath for 5 minutes. There were obtained 2.2 g of ethyl endo-3-(4-trifluoromethyl)-5,5a,6,6a-tetrahydro-4H-cyclopropa[g]-1,2-benzisoxazole-6-carboxylate of melting point 68° C.

The starting material was prepared as follows:

(A) A solution of 5 g (27.5 mmol) of ethyl endo/exo-2-oxobicyclo[4:1:0]heptanecarboxylate (endo:exo ratio 1:1) and 4.77 g (67 mmol) of pyrrolidine in 50 ml of dry benzene was heated under reflux for 3 hours until water was no longer produced. The benzene was removed and replaced by 30 ml of dry diethyl ether.

(B) A solution of 2.26 g (22 mmol) of triethylamine in 10 ml of dry diethyl ether was added at 5° C. over a period of 0.25 hour while stirring to a solution of 4.92 g (22 mmol) of 4-trifluoromethylbenzenecarboximidoyl N-hydroxy chloride in 20 ml of dry diethyl ether. After 1 hour, the precipitated triethylamine hydrochloride was filtered off and washed with 20 ml of dry diethyl ether which was subsequently combined with the filtrate.

(C) The solution prepared according to paragraph (B) was added to the solution prepared according to paragraph (A). After 14 hours, the mixture was filtered and extracted o three times with 2N hydrochloric acid each time. The combined aqueous-acidic extracts were made basic with 2N sodium carbonate solution and extracted with diethyl ether. After chromatography on silica gel using ethyl acetate/hexane (1:2) for the elution, there were firstly eluted 3 g of ethyl endo-3-(4-trifluoromethylphenyl)-3a,5,5a,6,6a,6b-hexahydro-6b-pyrrolidino-4H-cyclopropa[g]-1,2-benzioxazole-6-carboxylate [MS: m/e 422 (M)+] and subsequently 3 g of ethyl exo-3-(4-trifluoromethylphenyl)-3a,5,5a,6,6a,6b-hexahydro-6b-pyrrolidino-4H-cycloprop[g]-1,2-benzisoxazole-6-carboxylate; MS: m/e 422 (M)+.

EXAMPLE 90

2.2 g of ethyl endo-3-(4-trifluoromethylphenyl)-5,5a,6,6a-tetrahydro-4H-cyclopropa[g]-1,2-benzisoxazole-6 -carboxylate were heated under reflux for 4 hours with 2.6 g of sodium hydroxide in 15 ml of water and 200 ml of methanol. Acidification with 2N hydrochloric acid and recrystallization from methanol gave 1.9 g of endo-3-(4-trifluoromethylphenyl)-5,5a,6,6a-tetrahydro-4H-cyclopropa[g]-1,2-benzisoxazole-6-carboxylic acid of melting point 209°–211° C.

EXAMPLE 91

1 g (4.93 mmol) of m-chloroperbenzoic acid in 15 ml of chloroform was added over a period of 5 minutes to a solution of 2 g (4.74 mmol) of ethyl exo-3-(4-trifluoromethylphenyl)-3a,5,5a,6,6a,6b-hexahydro-6b-pyrrolidino-4H-cyclopropa[g]-1,2-benzisoxazole-6-carboxylate in 10 ml of chloroform. After 16 hours, the m-chlorobenzoic acid was removed by filtration and the filtrate was washed with dilute sodium bicarbonate solution. The solvent was removed and the resulting crude ethyl exo-3-(4-trifluoromethylphenyl)-3a,5,5a,6-,6a,6b-hexahydro-6b-(N-oxido-1-pyrrolidinyl)-4H-cyclopropa[g]-1,2-benzisoxazole-6-carboxylate was heated at 120° C. in an oil bath for 5 minutes. There were thus obtained 1.3 g of ethyl exo-3-(4-trifluoromethylphenyl)-5,5a,6,6a-tetrahydro-4H-cyclopropa[g]-1,2-benzisoxazole-6-carboxylate of melting point 132° C.

EXAMPLE 92

1.3 g of ethyl exo-3-(4-trifluoromethylphenyl)-5,5a,6-,6a-tetrahydro-4H-cyclopropa[g]-1,2-benzisoxazole-6-carboxylate were heated under reflux for 4 hours with 1.54 g of sodium hydroxide in 10 ml of water and 120 ml of methanol. Acidification with 2N hydrochloric acid and recrystallization from methanol gave 0.9 g of exo-3-(4-trifluoromethylphenyl)-5,5a,6,6a-tetrahydro-4H-cyclopropa[g]-1,2-benzisoxazole-6-carboxylic acid of melting point 225° C.

The following Examples illustrate pharmaceutical preparations containing compounds of formula I and pharmaceutically acceptable salts of such compounds in which one of $R^1$ and $R^2$ is carboxy and the other is hydrogen with bases as the active ingredient.

EXAMPLE A

Tablets containing the following ingredients may be produced in a conventional manner:

| Ingredient | Per tablet |
| --- | --- |
| Active ingredient of Formula I or salt thereof | 50 mg |
| Lactose | 120 mg |
| Maize starch | 75 mg |
| Talc | 4 mg |
| Magnesium stearate | 1 mg |
| Tablet weight | 250 mg |

EXAMPLE B

Capsules containing the following ingredients can be produced in a conventional manner:

| Ingredient | Per capsule |
| --- | --- |
| Active ingredient of formula I or salt thereof | 100 mg |
| Lactose | 150 mg |
| Maize starch | 20 mg |
| Talc | 5 mg |
| Capsule fill weight | 275 mg |

We claim:

1. A compound of the formula

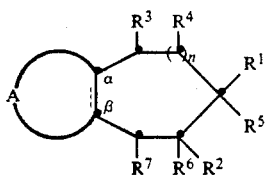

I wherein A taken together with the two carbon atoms denoted as α and β signifies a group of the formula

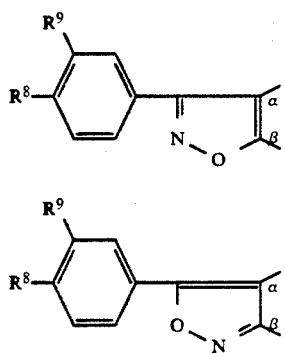

and the dotted line is the double bond present in formula (i); and wherein n is zero, 1, 2 or 3, one of $R^1$ and $R^2$ is carboxy or $C_{1-6}$-alkoxycarbonyl and the other is hydrogen, $R^3$ is hydrogen, $C_{1-6}$-alkyl, $C_{1-6}$-alkoxy, phenoxy or naphthyloxy group which is optionally substituted by one or more substituents selected from halogen, $C_{1-6}$-alkyl and $C_{1-6}$-alkoxy, azido, cyano or $C_{1-6}$-alkylthio, $R^4$, $R^5$, $R^6$ and $R^7$ each independently, are hydrogen, or $C_{1-6}$-alkyl or, when $R^1$ is carboxy or $C_{1-6}$-alkoxycarbonyl and n is 1, $R^4$ and $R^6$ taken together can be a carbon-carbon bond or, when $R^2$ is carboxy or $C_{1-6}$-alkoxycarbonyl, $R^5$ and $R^7$ taken together can be a carbon-carbon bond, $R^8$ is halogen, $C_{1-6}$-alkyl, $C_{1-6}$-haloalkyl or $C_{1-6}$-alkoxy and $R^9$ is hydrogen, halogen, $C_{1-6}$-alkyl or $C_{1-6}$-alkoxy, or a pharmaceutically acceptable salt of a compound of formula I in which one of $R^1$ and $R^2$ is carboxy and the other is hydrogen.

2. A compound according to claim 1, wherein $R^3$ is hydrogen, $C_{1-6}$-alkyl, $C_{1-6}$-alkoxy, phenoxy or naphthyloxy group which is optionally substituted by one or more substituents selected from halogen $C_{1-6}$-alkyl and $C_{1-6}$-alkoxy, or azido.

3. A compound according to claim 1, wherein A taken together with the two carbon atoms denoted as α and β is a group of formula (i).

4. A compound according to claim 3, wherein n is zero or 1.

5. A compound according to claim 4, wherein one of $R^1$ and $R^2$ is carboxy and the other is hydrogen.

6. A compound according to claim 5, wherein $R^3$ is hydrogen, $C_{1-6}$-alkyl, $C_{1-6}$-alkoxy or $C_{1-6}$-alkylthio.

7. A compound according to claim 6, wherein $R^3$ is hydrogen, methyl, methoxy or methylthio.

8. A compound according to claim 6, wherein $R^4$, $R^5$, $R^6$ and $R^7$ each is hydrogen or, when $R^2$ is carboxy, $R^5$ and $R^7$ taken together are a carbon-carbon bond and $R^4$ and $R^6$ each, independently, are hydrogen or $C_{1-6}$-alkyl.

9. A compound according to claim 7, wherein $R^8$ is halogen or alkoxy and $R^9$ is hydrogen.

10. A compound according to claim 9, wherein $R^8$ is chlorine or methoxy.

11. The compound according to claim 1, (+)-3-(4-chlorophenyl)-5,6,7,8-tetrahydro-4H-cyclohept[d]isoxazole-6-carboxylic acid.

12. The compound according to claim 1, 3-(4-chlorophenyl)-5,6,7,8-tetrahydro-4H-cyclohept[d]isoxazole-7-carboxylic acid.

13. The compound according to claim 1, endo-3-(4-chlorophenyl)-5,5a,6,6a-tetrahydro-4H-cyclopropa[g]-1,2-benzisoxazole-6-carboxylic acid.

14. The compound according to claim 1, trans-3-(4-chlorophenyl)-5,6,7,8-tetrahydro-4-methoxy-4H-cyclohept[d]isoxazole-7-carboxylic acid.

15. The compound according to claim 1, trans-3-(4-chlorophenyl)-5,6,7,8-tetrahydro-4-methyl-4H-cyclohept[d]isoxazole-7-carboxylic acid.

16. The compound according to claim 1, endo-3-(4-chlorophenyl)-6-ethyl-5,5a,6,6a-tetrahydro-4H-cyclopropa[g]-1,2-benzisoxazole-6-carboxylic acid.

17. A pharmaceutical composition for the treatment of rheumatoid arthritis, inflammatory respiratory diseases, inflammatory bowel disease and shock containing an effective amount of a compound of the formula

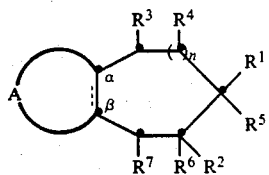

wherein A taken together with two carbon atoms denoted as α and β is a group of the formula

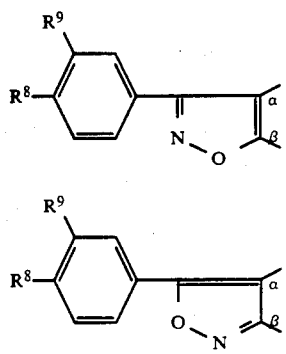

and the dotted line is the double bond present in formula (i); and wherein n is zero, 1, 2 or 3, one of $R^1$ and $R^2$ is carboxy or $C_{1-6}$-alkoxycarbonyl and the other is hydrogen, $R^3$ is hydrogen, $C_{1-6}$-alkyl, $C_{1-6}$-alkoxy, phenoxy or naphthyloxy group which is optionally substituted by one or more substituents selected from halogen, $C_{1-6}$-alkyl and $C_{1-6}$-alkoxy, azido, cyano or $C_{1-6}$-alkylthio, $R^4$, $R^5$, $R^6$ and $R^7$ each, independently is hydrogen or $C_{1-6}$-alkyl, or when $R^1$ is carboxy or $C_{1-6}$-alkoxycarbonyl and n is 1, $R^4$ and $R^6$ taken together can be a carbon-carbon bond or when $R^2$ is carboxy or $C_{1-6}$-alkoxycarbonyl, $R^5$ and $R^7$ taken together can be a carbon-carbon bond, $R^8$ is halogen, $C_{1-6}$-alkyl, $C_{1-6}$-haloalkyl or $C_{1-6}$-alkoxy and $R^9$ is hydrogen, halogen, $C_{1-6}$-alkyl or $C_{1-6}$-alkoxy, or a pharmaceutically acceptable salt of a compound of the formula I in which one of $R^1$ and $R^2$ is carboxy and the other is hydrogen and an inert carrier.

18. A pharmaceutical composition according to claim 17 for the treatment of rheumatoid arthritis.

19. A method of treating rheumatoid arthritis, inflammatory respiratory diseases, inflammatory bowel disease and shock which comprises administering to a host in need of such treatment as effective amount of a compound of the formula

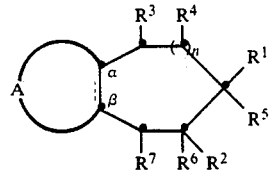

wherein A taken together with two carbon atoms denoted as α and β is a group of the formula

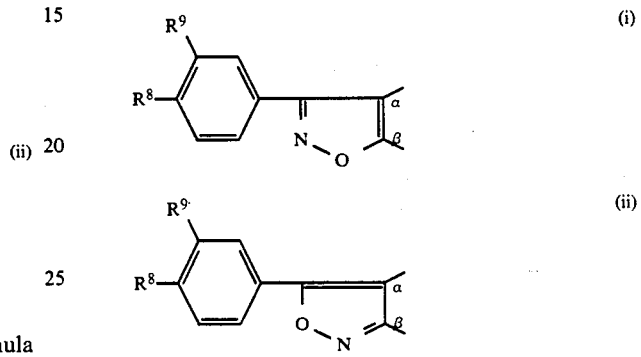

and the dotted line is the double bond present in formula (i); and wherein n is zero, 1, 2 or 3, one of $R^1$ and $R^2$ is carboxy or $C_{1-6}$-alkoxycarbonyl and the other is hydrogen, $R^3$ is hydrogen, $C_{1-6}$-alkyl, $C_{1-6}$-alkoxy, phenoxy or naphthyloxy group which is optionally substituted by one or more substituents selected from halogen, $C_{1-6}$-alkyl and $C_{1-6}$-alkoxy, azido, cyano or $C_{1-6}$-alkylthio, $R^4$, $R^5$, $R^6$ and $R^7$ each, independently, is hydrogen or $C_{1-6}$-alkyl or, when $R^1$ is carboxy or $C_{1-6}$-alkoxycarbonyl and n is 1, $R^4$ and $R^6$ taken together can be a carbon-carbon bond or when $R^2$ is carboxy or $C_{1-6}$-alkoxycarbonyl, $R^5$ and $R^7$ taken together can be a carbon-carbon bond, $R^8$ is halogen, $C_{1-6}$-alkyl, $C_{1-6}$-haloalkyl or $C_{1-6}$-alkoxy and $R^9$ is hydrogen, halogen, $C_{1-6}$-alkyl or $C_{1-6}$-alkoxy, or a pharmaceutically acceptable salt of a compound of formula I in which one of $R^1$ and $R^2$ is carboxy and the other is hydrogen.

20. A method according to claim 19 of treating rheumatoid arthritis.

* * * * *